United States Patent [19]

Marcec et al.

[11] Patent Number: 5,016,467
[45] Date of Patent: May 21, 1991

[54] AUTOMATED FLOW RATE MACHINE

[75] Inventors: Jerome J. Marcec; James O. Phillips, both of Naperville; Albert T. Grzybowski, Diamond Lake, all of Ill.; Bohdan Grzybowski, Sarasota, Fla.

[73] Assignee: Amoco Corporation, Chicago, Ill.

[21] Appl. No.: 362,727

[22] Filed: Jun. 7, 1989

[51] Int. Cl.⁵ .......................................... G01N 11/06
[52] U.S. Cl. ..................................................... 73/56
[58] Field of Search .................................. 73/56, 55

[56] References Cited

U.S. PATENT DOCUMENTS

| 4,335,336 | 6/1982 | Myerholtz et al. | 73/56 |
| 4,680,958 | 7/1987 | Ruelle et al. | 73/56 |
| 4,882,930 | 11/1989 | Nagy et al. | 73/56 |

FOREIGN PATENT DOCUMENTS

| 210689 | 2/1987 | European Pat. Off. | 73/56 |
| 2140619 | 2/1973 | Fed. Rep. of Germany | 73/56 |
| 21542 | 2/1983 | Japan | 73/56 |
| 81545 | 4/1987 | Japan | 73/56 |

OTHER PUBLICATIONS

Preliminary Technical Information of Robotic Scientific, Inc. "Petron MI-200 Automatic Melt Index".
ASTM D 1238-82, "Flow Rates of Thermoplastics by Extrusion Plastometer", 1982.
Bulletin 2802 of Allen-Bradley Company, Line Scan Camera.

Primary Examiner—Hezron E. Williams
Assistant Examiner—Joseph W. Roskos
Attorney, Agent, or Firm—Robert G. Ladd; William H. Magidson; Ralph C. Medhurst

[57] ABSTRACT

An apparatus and method capable of automated flow rate measurements of thermoplastic polymers which includes mechanisms for automatically loading a test polymer into a test cavity of a heating block and mechanisms for automatically cleaning the test cavity and a piston rod movable therein. The test cavity can be provided in the heating block or can be defined by a sleeve/die insert which also serves as a sample receiving cavity and which is movable into and out of a heating block for carrying out a rheological test of polymer material received in the sleeve/die insert.

36 Claims, 21 Drawing Sheets

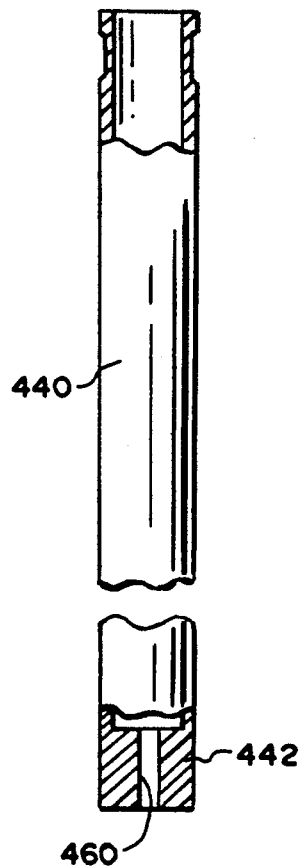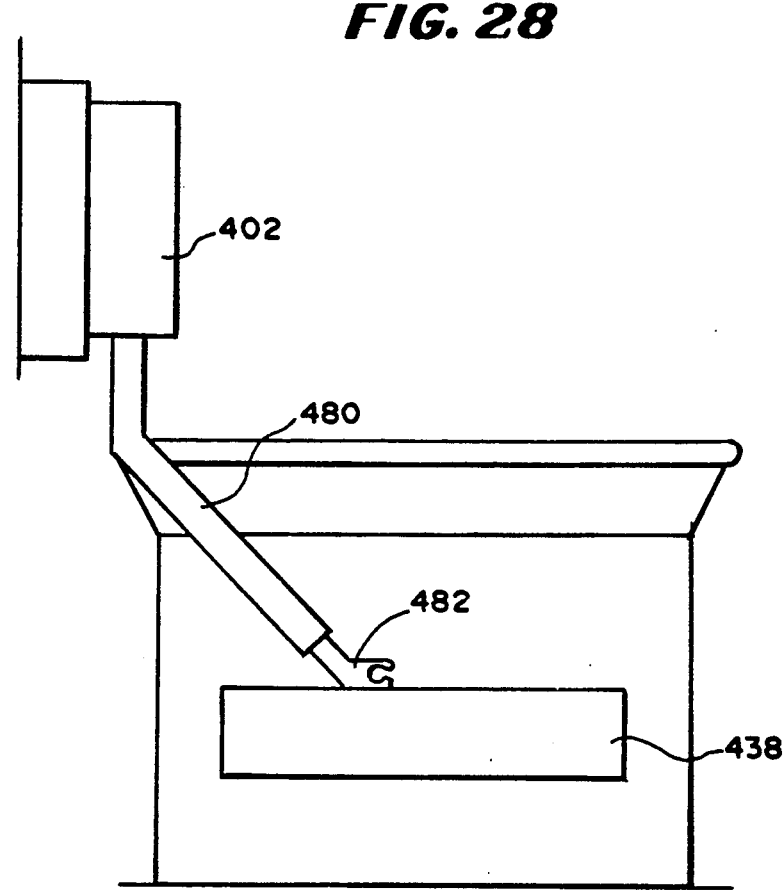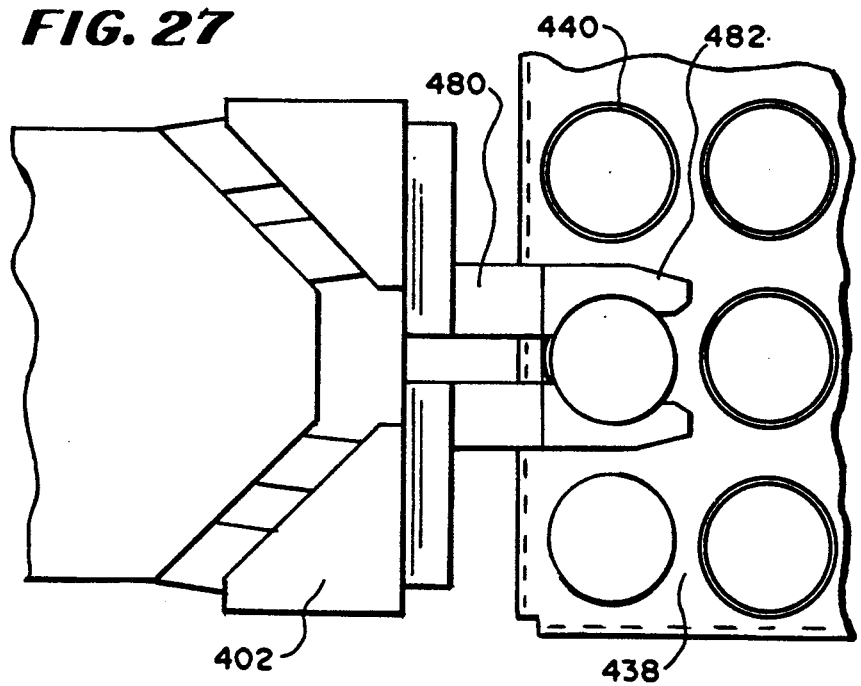

AUTOMATED FLOW RATE MACHINE

FIELD OF THE INVENTION

The present invention relates to an apparatus and method capable of automated flow rate measurements of different thermoplastic polymer resin samples in an automatic, accurate and repeatable manner. Additionally, the present invention relates to such an automated flow rate machine which includes mechanisms for automatically loading a test cavity in a heating block with sample and mechanisms for automatically cleaning the test cavity and a piston rod movable therein.

BACKGROUND OF THE INVENTION

Rheological testing of resinous polymeric materials to measure properties such as melt flow rate, melt index and die swell involves many operations and must be performed consistently test after test in order to obtain reproducible data. These properties, in turn, are commonly used to assist in selecting polymer or grades thereof for use in particular applications such as monitoring polymer production processes, and establishing suitable process conditions for these polymers. It is desirable, therefore, to eliminate inconsistencies that are inevitable, due to individual-to-individual variations in technique or because of fatigue of an individual operation over a period of time.

Improving the precision of rheological properties of thermoplastic materials has long been the goal of those concerned with the testing of thermoplastic materials, particularly the melt flow rate and melt index properties.

U.S. Pat. No. 4,680,958 discloses an apparatus for the fast determination of the rheological properties of thermoplastic polymers. The apparatus disclosed in this patent is operable to raise and lower a test weight over a test cavity. However, the disclosed apparatus is not operable to load the sample in the test cavity and to clean the test cavity after the test.

U.S. Pat. No. 4,335,336 discloses a method and device for automatically and instantaneously computing and displaying with high precision the flow rate of thermoplastic samples run in an extrusion plastometer in accordance with ASTM Method D 1238-86. The method and device comprise using a microcomputer and related circuitry to monitor and control the measurement process and subsequently compute the resulting flow rate. The disclosed apparatus is not suggested for loading the sample into the test cavity or for cleaning the test cavity after the test.

A bulletin of Robotic Scientific, Inc., P.O. Box 11037, Spring, Tex. 77391-1037 labeled as a technical information bulletin disclosed a robotic instrument which automatically measures the flow rate of extruded polymers according to ASTM Standard Test Method D 1238-86. The instrument consists of two, automatic extrusion plastometers equipped with carousels holding up to twenty-four sample cartridges each, and uses replaceable cartridges and pistons which conform to the specifications of the ASTM Standard. The bulletin does not suggest cleaning of the test cavity or pistons after the test.

The melt flow rate or "melt index" of thermoplastics as determined by ASTM Method D 1238-86 (current edition approved Oct. 31, 1986 and published December 1986; originally published as D 1238-65T; incorporated herein by reference), or foreign counterparts, is generally employed as a specification or inspection property.

It is a goal of the automated flow rate machine of the present invention to provide automatic testing and subsequent cleaning of the test cavity and the pistons utilized in carrying out the test to provide high precision and high reproducibility in the test data.

As will be described in greater detail hereinafter, in a preferred embodiment the automated flow rate of the present invention utilizes automated devices to perform various functions, thereby to enable the machine to perform a complete test from loading a sample into a test cavity of a heating block for carrying out the test and for subsequent cleaning at the end of the test of the test cavity and the piston used to determine rheological properties of a thermoplastic such as melt flow rate.

SUMMARY OF THE INVENTION

According to the invention there is provided apparatus for automated flow rate measurements of a polymer comprising:
a table;
at least one heating block attached to the table;
a test cavity positioned in the heating block, the test cavity having a cylindrical shape with an upper end of the test cavity defining an orifice for receiving the polymer and a lower end of the test cavity defining an extrusion die;
means for maintaining the heating block at a predetermined temperature;
means for receiving the polymer said means being removably attached to said table;
means for transferring the polymer from the polymer receiving means into the test cavity;
a piston rod having an upper collar fixed thereon, a lower knurled collar slidable thereon and a piston foot located at the end of the piston rod opposite to the upper collar;
means for holding and transferring said piston rod between said means and the test cavity;
at least one test weight;
means for holding and transferring said test weight between said means and the piston rod;
means for timing a sequence of stages of the flow rate measurement after the polymer has been received in the test cavity, the piston rod has been transferred to the test cavity, the test weight has been transferred to the piston rod and whereby the test weight acting on the piston rod causes the piston rod to move downwardly through the test cavity and to extrude the polymer through the extrusion die;
means for calculating the flow rate of the thermoplastic from the timed sequence of stages;
means for cleaning the test cavity said means attached to said table; and
means for cleaning the piston rod said means attached to said table.

Further according to the invention there is provided a method for making automated flow rate measurements of a polymer comprising the steps of:
maintaining a heating block at a predetermined temperature;
inserting polymer into a polymer receiving means;
placing polymer from the polymer receiving means into a test cavity in the heating block;
moving a piston rod into the test cavity;

timing a holding period of polymer in the heating block;

placing a test weight on the piston rod in the test cavity whereby the test weight acting on the piston rod causes the piston rod to move downwardly into the test cavity to move heated polymer therein;

measuring an amount of time between the beginning of the downward movement of the weighted piston rod and when the weighted piston rod has moved a predetermined distance downwardly into the test cavity;

calculating the flow rate using the amount of time measured and a factor corresponding to the polymer;

removing the piston rod from the test cavity;

cleaning the piston rod; and cleaning the test cavity in the heating block to prepare the heating block for another flow rate test.

The test cavity can be provided in the heating block or can be defined by a sleeve/die insert which also serves as a sample receiving cavity and which is movable into and out of a heating barrel for carrying out a rheological test of the polymer material received in the sleeve/die insert.

BRIEF DESCRIPTION OF THE DRAWINGS

FIG. 26 is a vertical sectional view through one empty sleeve/die insert which is received in a sleeve/die insert holder positioned in the machine shown in FIG. 25.

FIG. 27 is an enlarged top plan view of the cartesian movable overhead manipulator shown in FIG. 25 positioned with an end-of-arm tool thereon in engagement with a sleeve/die insert.

FIG. 28 is a fragmentary side view of the end-of-arm tool shown in FIG. 27.

DESCRIPTION OF THE PREFERRED EMBODIMENTS

Figure 1:
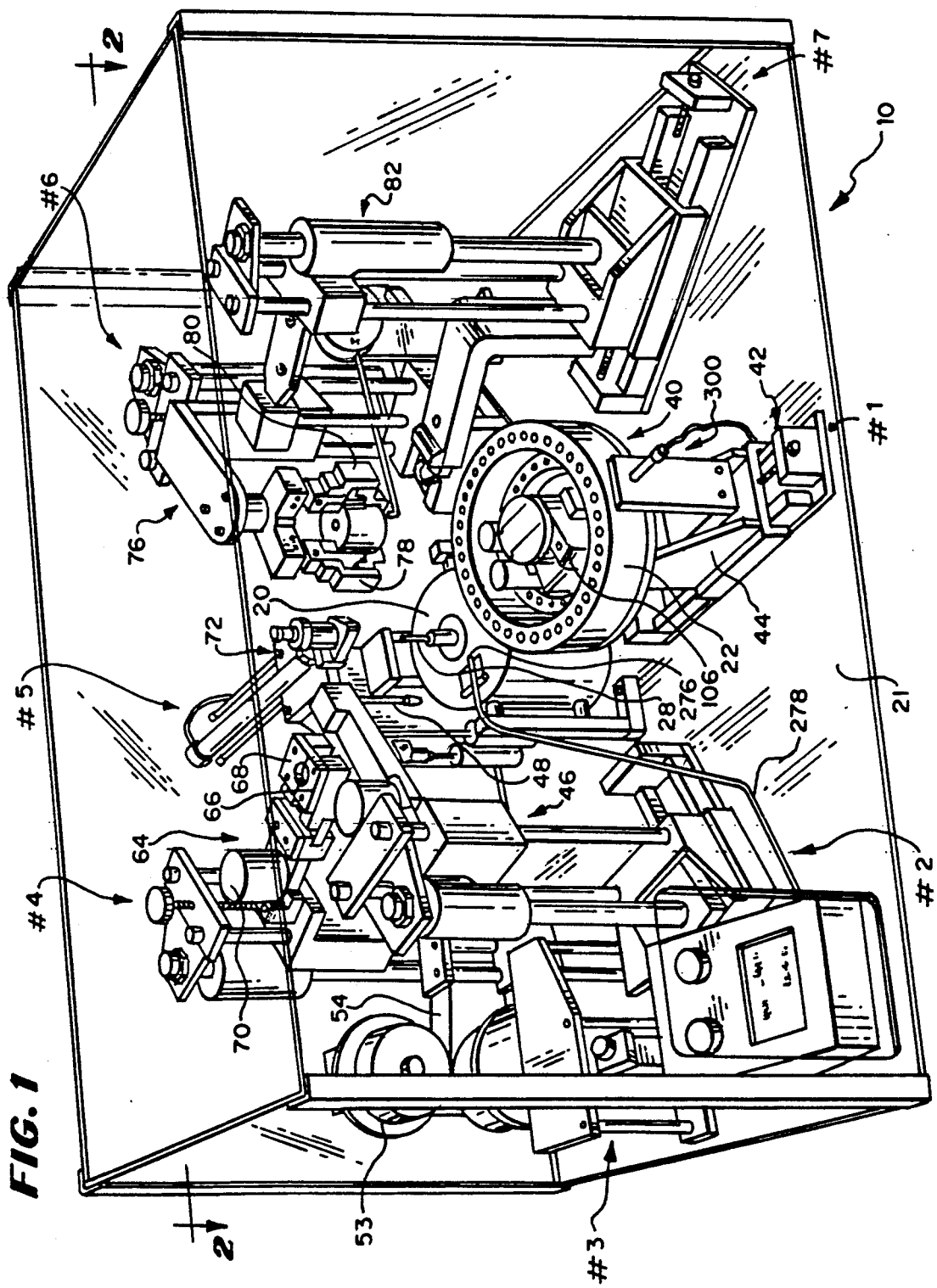
FIG. 1 is a perspective view of the automated flow rate machine of the present invention.

Referring to the drawings in greater detail, there is illustrated in FIG. 1 an automated flow rate machine 10 constructed according to the teachings of the present invention. The machine 10 includes multiple stations 1-7 which are located around a heating block 20 mounted on a table 21. Heating block 20 can be in the shape of a cylinder or a barrel. An embodiment of the present invention includes seven stations as described hereinbelow.

Various mechanisms are located at each of the multiple stations and are operated electrically or pneumatically for achieving testing of a sample of a plastic material. This includes taking a sample from a carousel 22 located at a station 1, inserting it in a test cavity 24 (FIG. 9) in the heating block 20, heating the heating block 20 with the sample therein as well as a piston rod 28 with a piston foot 26 (FIG. 9) at the lower end of the piston rod 28 (FIG. 9) situated over the sample in the test cavity 24 and then allowing a weight 30 (FIG. 11) to be mounted on the top of the piston rod 28 and to cause the same to move downwardly. The weight 30 will cause the piston foot 26 to move downwardly against the melted polymer and cause the melted polymer to flow through a die passageway 32 (FIG. 9) at the lower end of the test cavity 24 in the heating block 20.

Sensors, such as one or more limit switches or optical (infrared) sensors are provided, as will be described in greater detail hereinafter, for sensing when the weight 30 is placed on the piston rod 28 and when the weight 30 has travelled a predetermined distance. This time period of travel of the weight 30 on the piston rod 28 is captured and utilized to generate flow rate data following the test method set forth in ASTM D 1238-86. The figure of merit is grams per 10 minutes and is directly related to a parameter of the plastic material, such as the molecular weight of a thermoplastic.

In this way, the molecular weight or other properties of a thermoplastic (such as polyethylene or polypropylene) can be quickly and easily determined.

In order to enable the machine 10 to continuously carry out such tests, stations 3, 4, 5 and 7 are provided for facilitating cleaning of the piston foot 26, piston rod 28 and the test cavity 24.

As will be described in greater detail hereinafter, stations 3 and 4 are provided for cleaning the piston foot 26 and piston rod 28 and stations 5 and 7 are provided for cleaning the test cavity 24.

Figure 2:
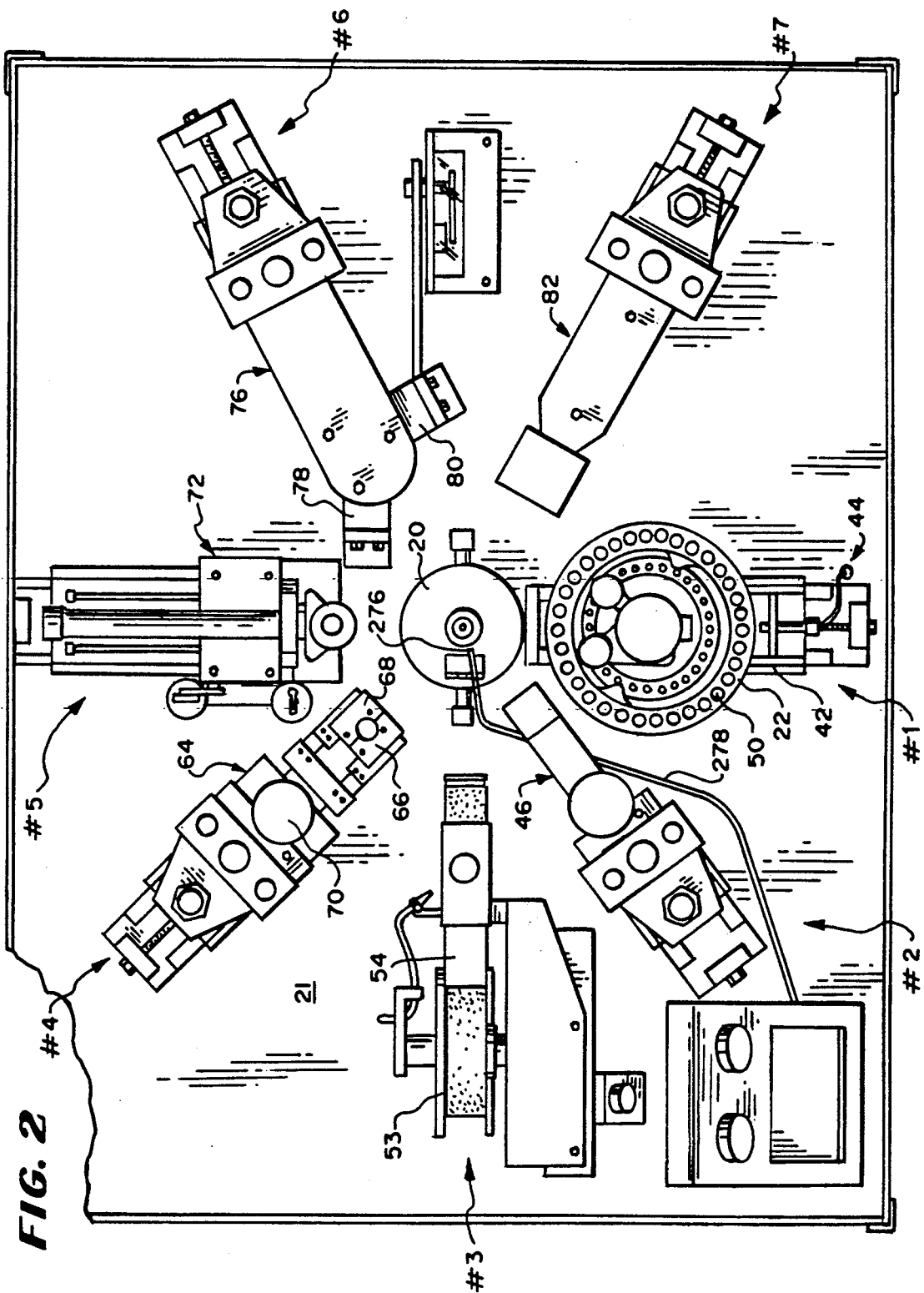
FIG. 2 is a top plan view of the machine shown in FIG. 1 and shows seven work stations of the machine positioned about a heating block of the machine.

FIG. 2 is a top plan view of the machine 10 shown in FIG. 1 and shows a carousel assembly 40 (FIG. 6) including the carousel 22 at station 1 and a mechanism 42 for horizontally moving a horizontally reciprocal carriage 44 mounting the carousel assembly 40.

Adjacent to station 1 is a station 2 which includes a tamping mechanism 46 which is movable from a home position shown in FIG. 2, inwardly over the heating barrel 20. The tamping mechanism 46 includes a tamping rod 48 (FIG. 7) which is movable up and down for tamping polymer from a sample receiving/holding cavity 50 (FIG. 5) in the carousel 22 (FIG. 5) of the carousel assembly 40 into the test cavity 24 in the heating block 20. The polymer initially can be in the form of pellets, chips, flakes, powder, fiber, film, etc.

At a station 3 a cleaning material reel 53 containing a strip 54 (FIG. 16) of cleaning material. The strip 54 is trained over a cleaning cavity 56 (FIG. 17) in a cleaning block 58 (FIG. 17). A nozzle 60 (FIG. 17) at the end of a liquid delivery line 62 (FIG. 17) is positioned at station 3 to eject an optional metered quantity of cleaning solvent, such as decahydronaphthalene for thermoplastics such as polypropylene, polyethylenes and polystyrene, against the tamping rod 48 or the piston rod 28 when either is positioned above the cleaning cavity 56.

At a station 4 there is provided an articulated piston rod holding mechanism 64 which is operable to move from its home position shown in FIG. 2 inwardly over the test cavity 24 for moving the piston rod 28. For this purpose, the articulated piston rod holding mechanism 64 includes first and second jaws 66 and 68 which are adapted to move laterally in a pivoting manner toward and away from each other to position the jaws 66 and 68 about the piston rod 28 and then to move them inwardly toward each other to grip the piston rod 28. The articulated piston rod holding mechanism 64 includes a pivoting mechanism 70 for rotating the jaws 66 and 68 to a position over station 3, as will be described in greater detail in connection with the description of FIG. 17.

At a station 5 there is located an applicator mechanism 72 which is operable to supply a piece 74 of cleaning material, (FIG. 19), such as a cotton patch, over the test cavity 24 in the heating block 20 for cleaning the test cavity 24.

Figure 11:
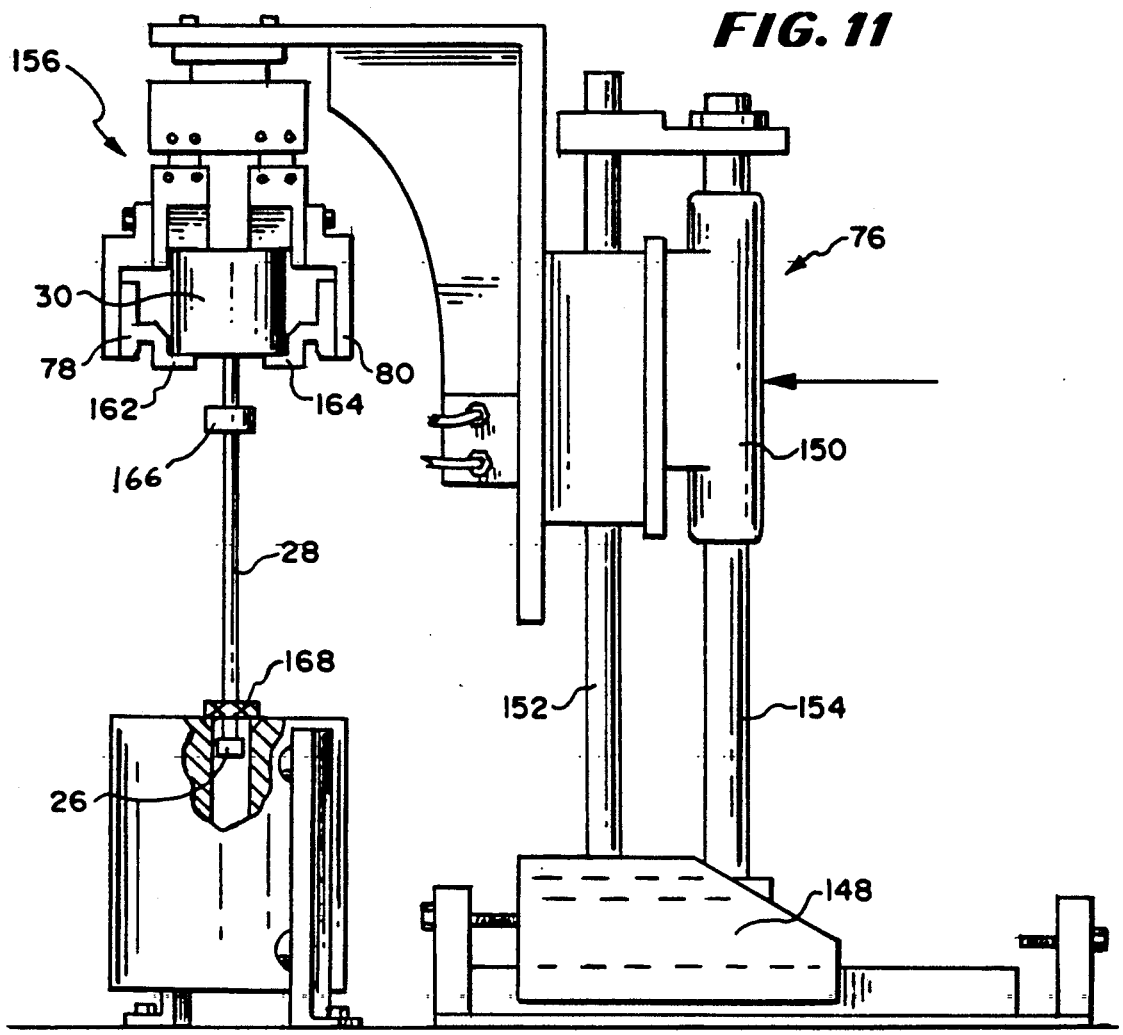
FIG. 11 is a side elevational view of a weight holding mechanism at station 6 shown in its extended position for positioning a weight on top of the piston rod received in the test cavity.

At a station 6 there is located a weight holding mechanism 76 which is operable to move to and from the position shown in FIG. 11 over the test cavity 24 and which has jaws 78, 80 for moving the weight 30 on top of the piston rod 28 when it is located in the test cavity 24 in the heating block 20.

Figure 20:
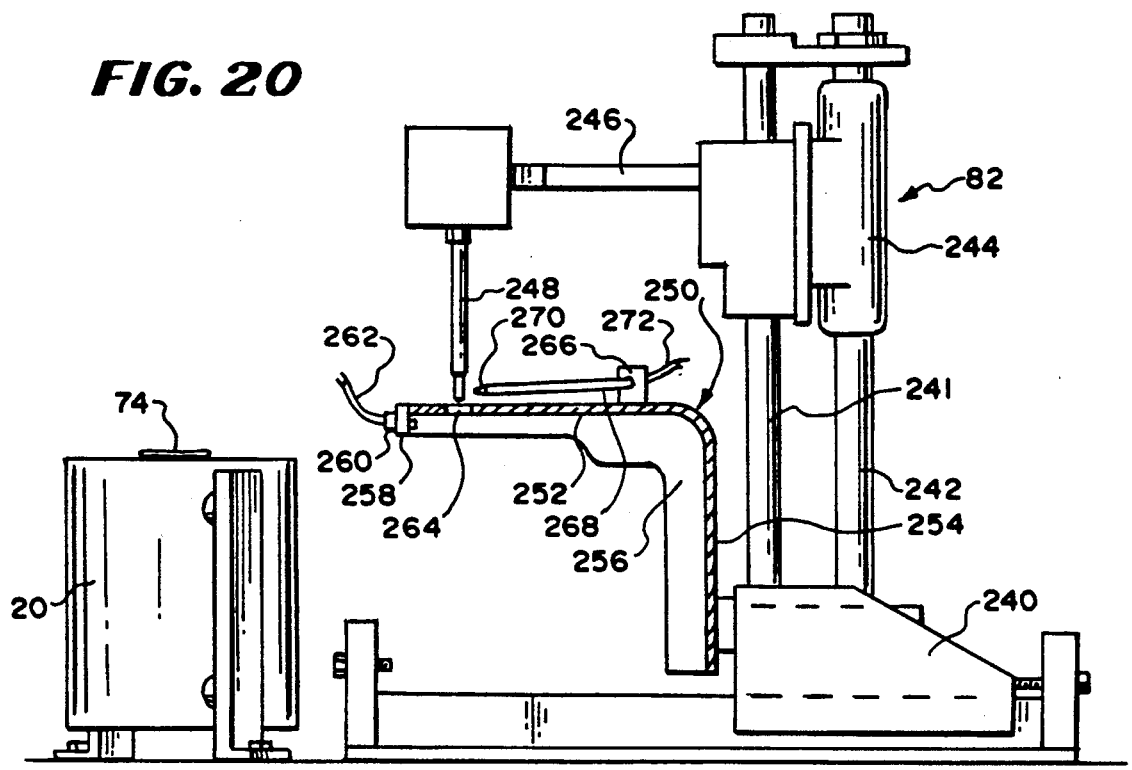
FIG. 20 is a side elevational view of a cavity cleaning mechanism at station 7 in its retracted position and shows the heating block with the cotton patch positioned over the test cavity therein.

At a station 7 is located a cavity cleaning mechanism 82 which is movable from and to the position shown in FIG. 20 inwardly over the heating block 20 for facilitating the cleaning of the test cavity 24 in the heating block 20 and for disposing of a used cleaning material piece 84 (FIG. 22) used in the cleaning procedure.

Figure 3:
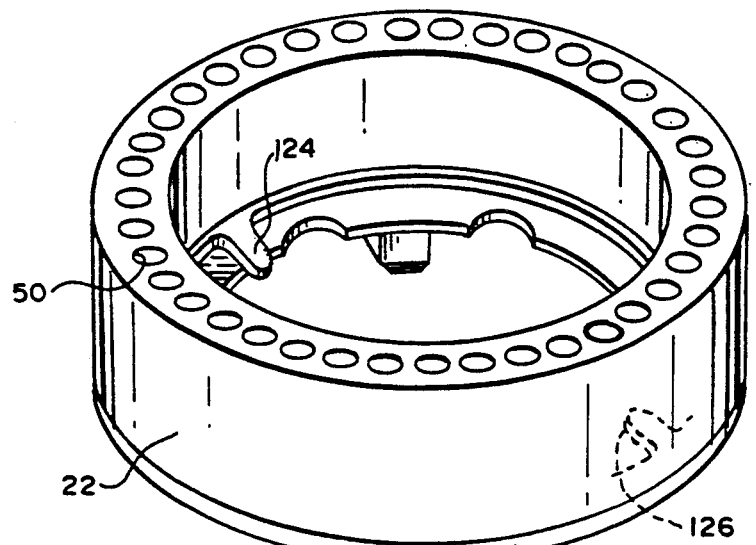
FIG. 3 is a perspective view of a sample holding carousel of a carousel assembly that is located at station 1.

Turning now to FIG. 3, there is shown therein a perspective view of the sample receiving carousel 22 having a plurality of the sample receiving/holding cylindrical cavities 50 located in a generally circular array. The carousel 22 of the carousel assembly 40 is positioned over a rotatable annular plate 88 which has two spaced apart grooves 90, 92 on the inner circumference thereof which permit two cylindrical blocks 94, 96 on a carousel drive mechanism 98 of the carousel assembly 40 to pass upwardly within the central space of the annular plate 88.

Figure 4:
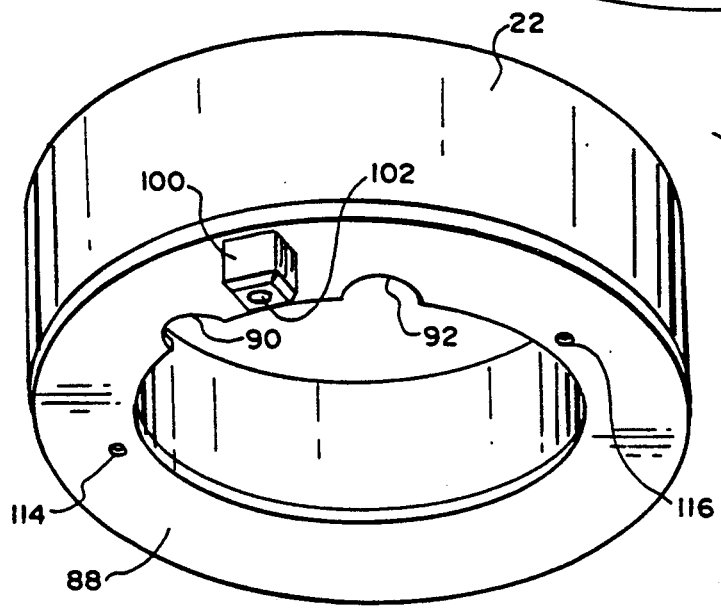
FIG. 4 is an exploded perspective view of the carousel assembly and shows a circular drive mechanism on which the carousel is received with the carousel positioned thereabove.
Figure 5:
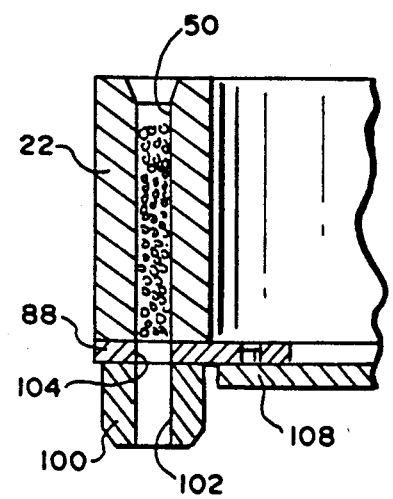
FIG. 5 is a fragmentary vertical sectional view through a sample receiving receptacle in the carousel shown in FIG. 3 with sample therein and positioned over an outlet in an annular plate located above the heating block.

As best shown in FIGS. 4 and 5, the annular plate 88 has a polymer dispensing block 100 located on the underside thereof.

As shown in FIG. 5, the polymer dispensing block 100 has a passageway 102 therethrough which mates with an orifice 104 extending through the plate 88. The carousel 22 is not fixed to the annular plate 88 but rather is movable (rotatably slidable) thereon so that respective ones of the sample receiving cylindrical cavities 50, such as the one shown in FIG. 5, can be positioned sequentially over the orifice 104 in the annular plate 88 so that samples can be moved through the annular plate 88 and the dispensing block 100 into the test cavity 24 in the heating block 20.

The carousel drive mechanism 98 includes a rotatable drive member 106 mounted for rotation on a base plate 108 as shown in FIG. 4. The base plate 108 is fixed to the horizontally reciprocal carriage 42 (FIG. 1) and has two pins 110 and 112 therein (FIG. 4) which are adapted to be received in two holes 114 and 116 in the annular plate 88. The cooperation between the pins 110 and 112 and the holes 114 and 116 serves two functions, first to properly locate the annular plate 88 relative to the carriage 42 (FIG. 6) on which the carousel assembly 40 is mounted and second to hold the annular plate 88 on the base plate 108 against rotation when the rotatable drive member 106 is rotated.

To properly locate the carousel 22 at the beginning of a test run and to know when the carousel 22 has been rotated a full 360 degrees, the rotatable drive member 106 has two spaced apart axially extended grooves 120, 122.

As shown in FIG. 3, extending inwardly from a lower inner edge of the carousel 22 are two detents 124 and 126 which are adapted to be received in the grooves 120 and 122 in the drive member 106 shown in FIG. 4.

In use, the annular plate 88 is positioned beneath the carousel 22. Then numbered samples are positioned within numbered sample receiving cavities 50 in the carousel 22. The annular plate 88 prevents the sample from falling through the cavities 50, since it forms a bottom for each of the cavities 50. Then, this assembly is placed on top of the carousel drive mechanism 98 with the two pins 110 and 112 (FIG. 4) on the base plate 108 being received in the two holes 114 and 116 (FIG. 4) on the annular plate 88 and with the cylindrical blocks 94, 96 (FIG. 4) passing through the notches 90, 92 (FIG. 4) in the annular plate 88. At the same time, the detents 124 and 126 (FIG. 3) extending inwardly from the carousel 22 at the bottom thereof engage in respective ones of the axially extending groves 120, 122 (FIG. 4) in the drive member 106. Then, in use, the drive member 106 is indexed sequentially to move sequentially each sample containing cavity 50 over the sample dispensing block 100.

Figure 6:
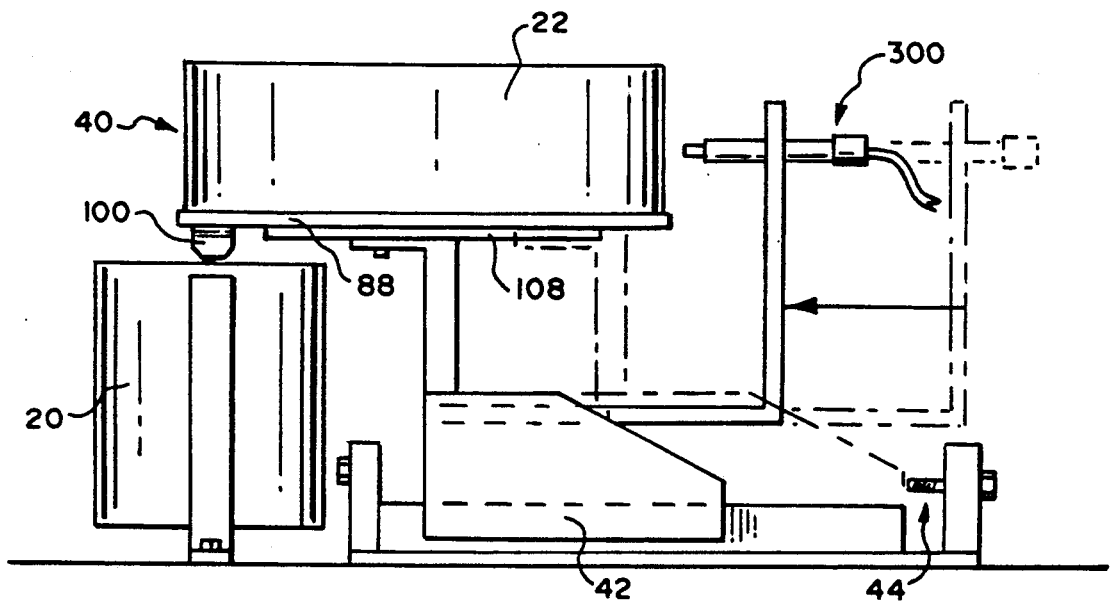
FIG. 6 is a side elevational view of the carousel assembly located over the heating block.

Turning now to FIG. 6, it will be seen that the carousel assembly 40 is mounted on the carriage 42 which is movable from a retracted position (shown in phantom) to an extended position shown in FIG. 6 where the sample dispensing block 100 is located over the test cavity 24 (FIG. 10) in the heating block 20.

Figure 7:
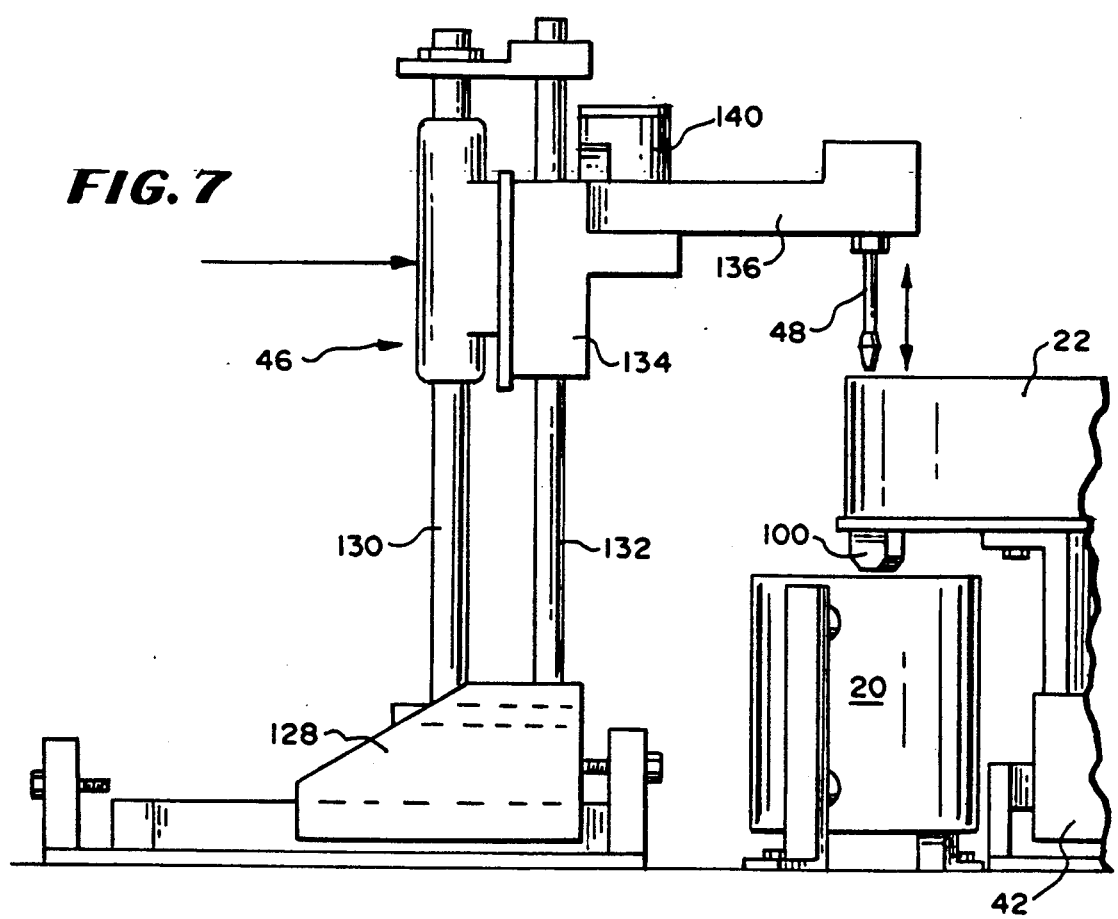
FIG. 7 is a side elevational view of a tamping mechanism at station 2 moved to a position over the carousel assembly and heating block.

With the carousel 22 located over the test cavity 24, as shown in FIG. 6, the tamping mechanism 46 at the station 2 is moved from its retracted position to an extended position, as shown in FIG. 7 where the tamping mechanism 46 is shown mounted on a horizontally reciprocal carriage 128. The tamping mechanism 46 includes at least two upright guide bars 130 and 132 on which is mounted a vertically reciprocating mechanism 134. The vertically reciprocating mechanism 134 has an outwardly extending arm 136 that has the tamping rod 48 depending from a distal end thereof. Once the tamping rod 48 is in the position shown in FIG. 7, located over a sample receiving cavity 50 (FIG. 5) that is positioned over the dispensing block 100 which in turn is positioned over the test cavity 24 (FIG. 10) in the heating block 20, the vertically reciprocating mechanism 134 is operated by a control circuit 138 (FIG. 23), to be described in greater detail hereinafter, upwardly and downwardly to tap or tamp the polymer sample in the sample receiving cavity 50 through the dispensing block 100 into the test cavity 24 in the heating block 20.

Figure 8:
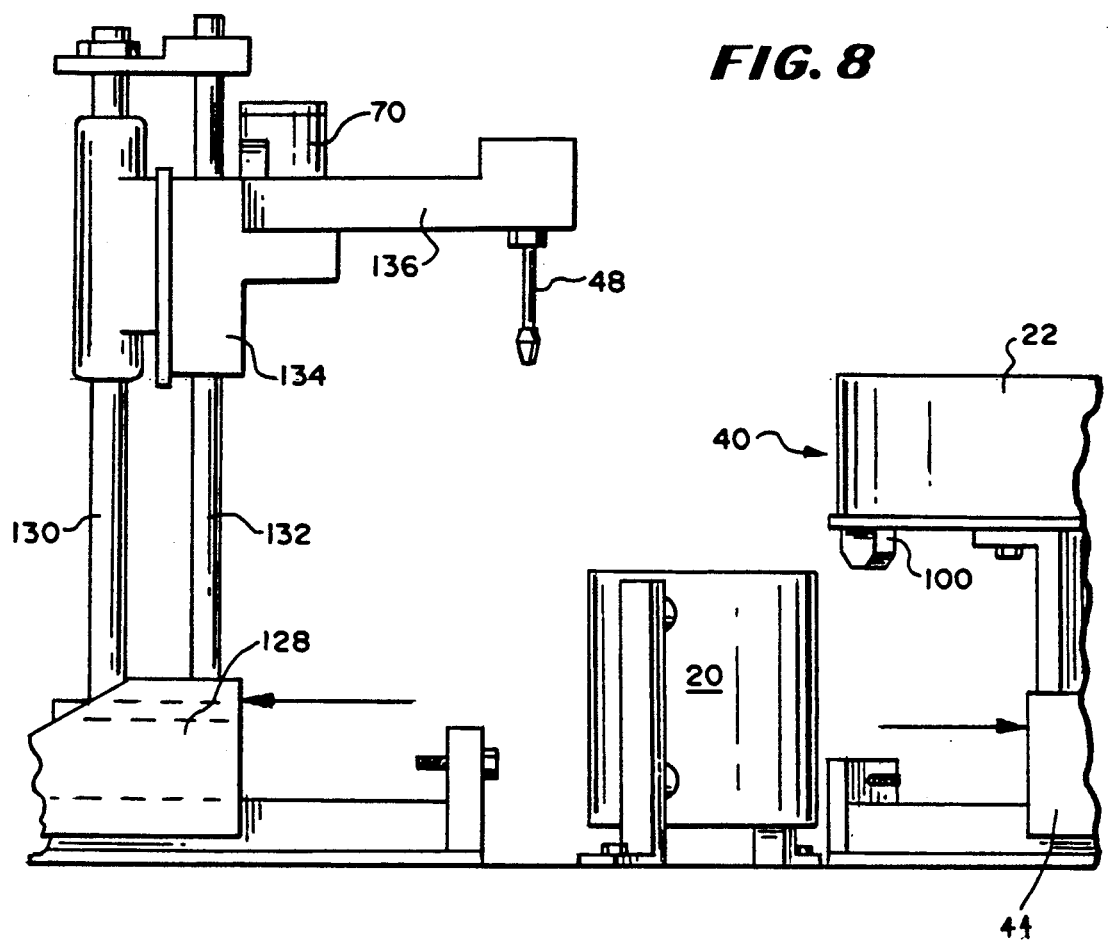
FIG. 8 is a side elevational view of the test barrel showing the carousel assembly being retracted to station 1 and the tamping mechanism being retracted to station 2.

After the sample of polymer has been inserted in the test cavity 24, the horizontally reciprocal carriage 128 at station 2 is retracted, as shown in FIG. 8. Although not shown, it is to be understood that a pivoting mechanism 140 on the vertically reciprocating mechanism 134 is operated to rotate the tamping rod 48 over the strip 54 of cleaning material where the tamping rod 48 is lowered into the cleaning cavity 56 in the cleaning block 58 with the strip 54 and the cleaning block 58 is rotated to clean the tamping rod 48.

Figure 10:
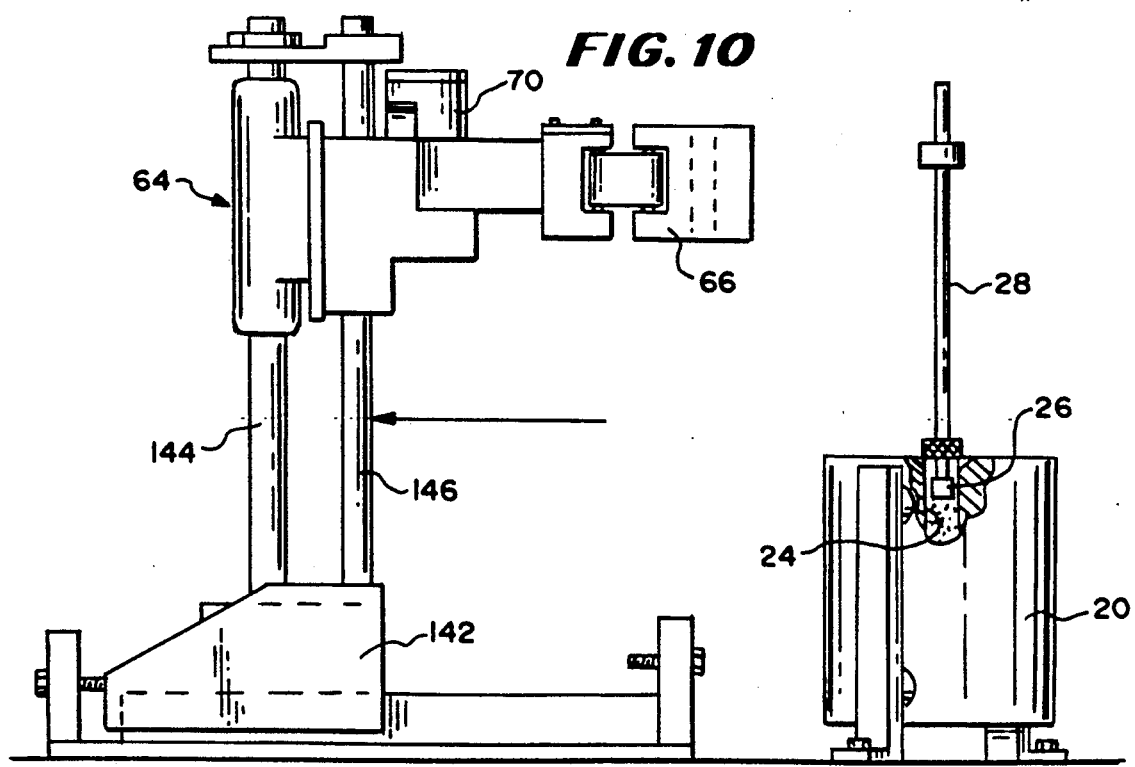
FIG. 10 is a side elevational view of the piston rod holding mechanism at station 4 after it has placed a piston rod in the heating block and has retracted to its home position.
Figure 9:
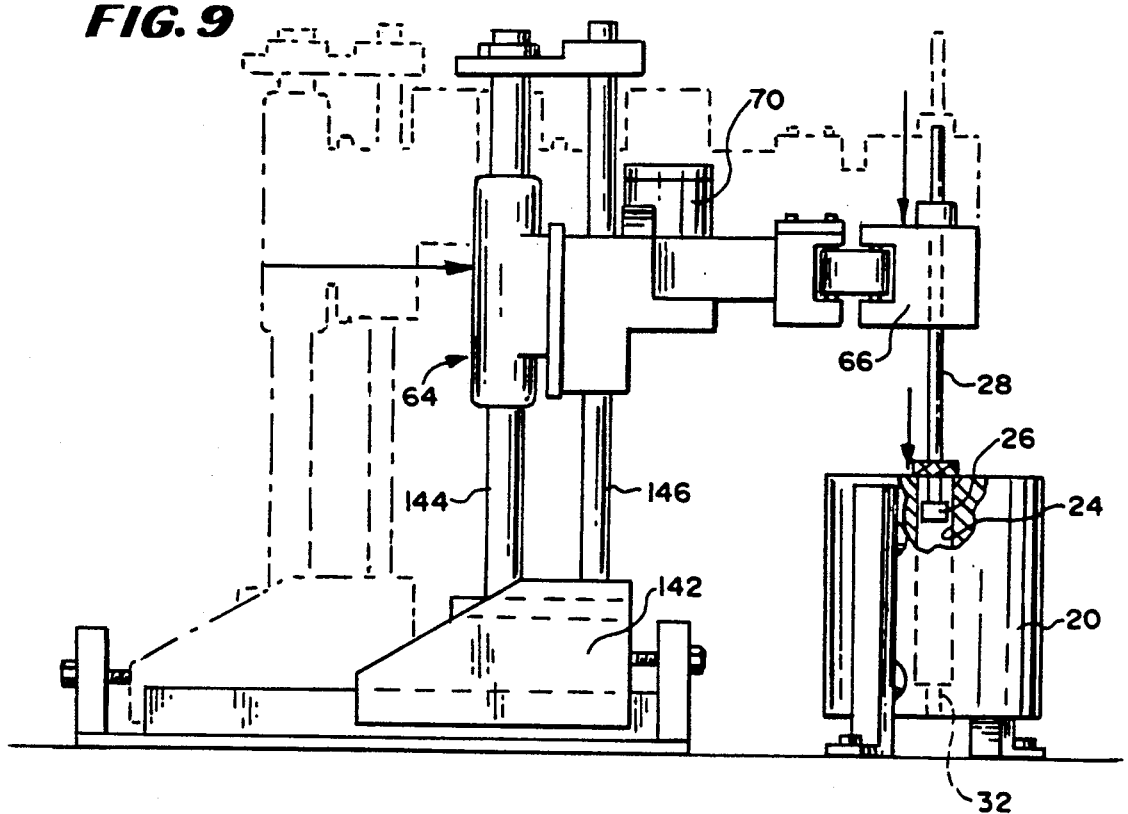
FIG. 9 is a side elevational view of an articulated piston rod holding mechanism in its extended position grasping a piston rod for moving the piston rod down to pack a test cavity in the heating barrel.

Next, as shown in FIGS. 9 and 10, the articulated piston rod holding mechanism 64 at station 4 is moved on a horizontally reciprocal carriage 142 from its home position, inwardly of the machine 10 to a position over the test cavity 24. The articulated mechanism 64 has the piston rod 28 clamped between the jaws 66 and 68 (FIGS. 1 and 2) thereof and such mechanism 64 is moved downwardly on at least two guide bars 144 and 146, to position the piston foot 26 at the lower end of the piston rod 28 in the test cavity 24 in the heating block 20. Then the articulated mechanism 64 opens the jaws 66 and 68 (FIGS. 1 and 2) and is retracted on the carriage 142 to its home position, as shown in FIG. 10.

Now a timing period is initiated during which the heating block 20 is heated by a heating element (not shown) associated with the heating block 20 to heat the polymer material to be tested to its melting point and at the same time the piston foot 26 is heated. This period can vary from 90 seconds to 10 minutes and is typically six minutes. The heating is controlled by a temperature sensor (not shown) associated with the heating block 20.

After the articulated mechanism 64 has been retracted as shown in FIG. 10, the weight holding mechanism 76 is moved from a home position to a position over the piston rod 28 by a horizontally movable carriage 148 as shown in FIG. 11. The weight holding mechanism 76 includes not only the horizontally reciprocal carriage 148 but also a vertically reciprocal carriage 150. The vertically reciprocal carriage 150 is mounted for vertical reciprocation on at least two guide bars 152 and 154, as shown in FIG. 11. Fixed to, and extending outwardly from, the vertically reciprocal carriage 150 is a L-shaped jaw assembly 156 having two jaws 78 and 80 which are each mounted for rotation toward and away from each other. Each of the jaws 78 and 80 has a lower flange 162, 164 which is positioned under the cylindrical weight 30.

As shown in FIG. 11 (and other of the Figures), the piston rod 28 has an upper collar 166 fixed thereon and a lower knurled collar 168 which is slidable thereon. The lower collar 168 serves to close off the upper end of the test cavity 24 so that the piston rod 28 is properly centered and the heated atmosphere in the test cavity 24, heating the piston foot 26 and the polymer material therein, does not escape from the test cavity 24 thereby to maintain the piston foot 26 and the melted polymer material at a substantially constant temperature.

Figure 12:
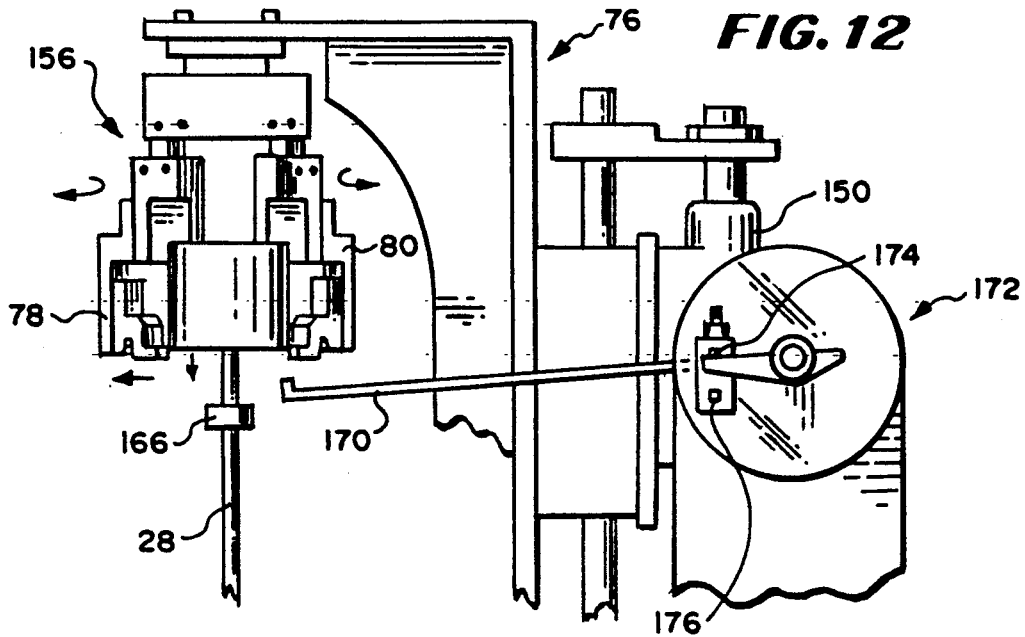
FIG. 12 is a fragmentary side elevational view of the weight holding mechanism showing the release of the weight onto the piston rod by the weight holding mechanism.

Now after the piston foot 26 and melted polymer material have been heated to the desired temperature for the desired period, such as six minutes, the jaws 78 and 80 are rotated away from each other to release the weight 30 which has a central throughbore therethrough. The weight 30 will fall downwardly, on the piston rod 28 against the upper collar 166. As the weight 30 falls, it will engage a lever arm 170 of a switch timing mechanism 172 which is mounted at station 6 as shown in FIG. 12 but which is omitted from the view shown in FIG. 11.

When the weight 30 hits the arm 170, it starts a timing period. The switch timing mechanism 172 includes two contact switches such that a circuit is opened when the arm 170 moves downwardly from an upper contact switch 174 (FIG. 12) and a circuit is closed when the arm 170 reaches a lower contact switch 176 (FIG. 12). Also, a noncontact system can be employed in place of the arm 170 and the switch timing mechanism 172.

Figure 13:
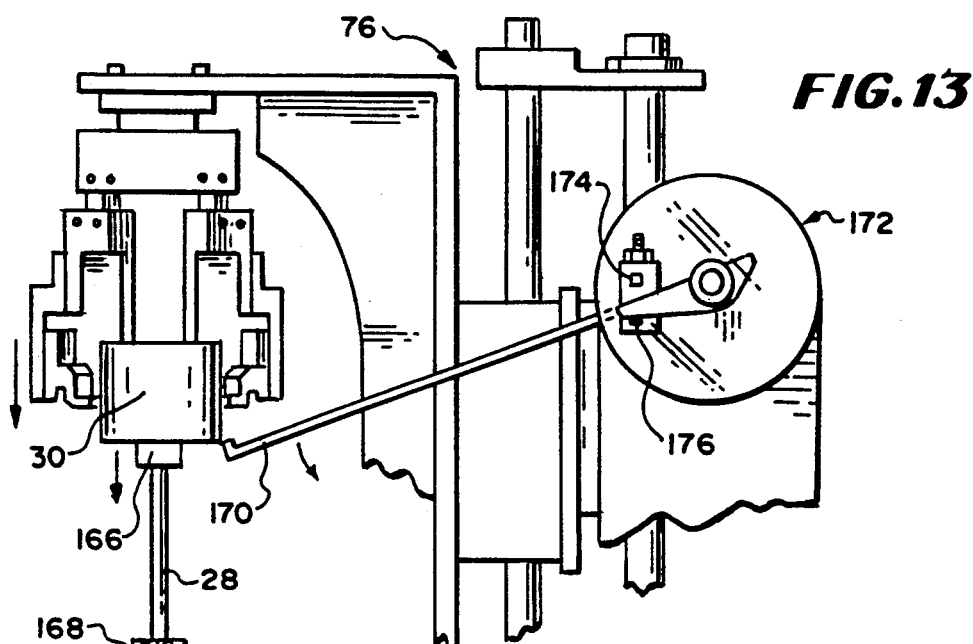
FIG. 13 is a fragmentary side elevational view of the weight holding mechanism with the weight positioned above the piston rod received in the test cavity and shows a switch which is actuated when the weight moves down past the switch.
Figure 14:
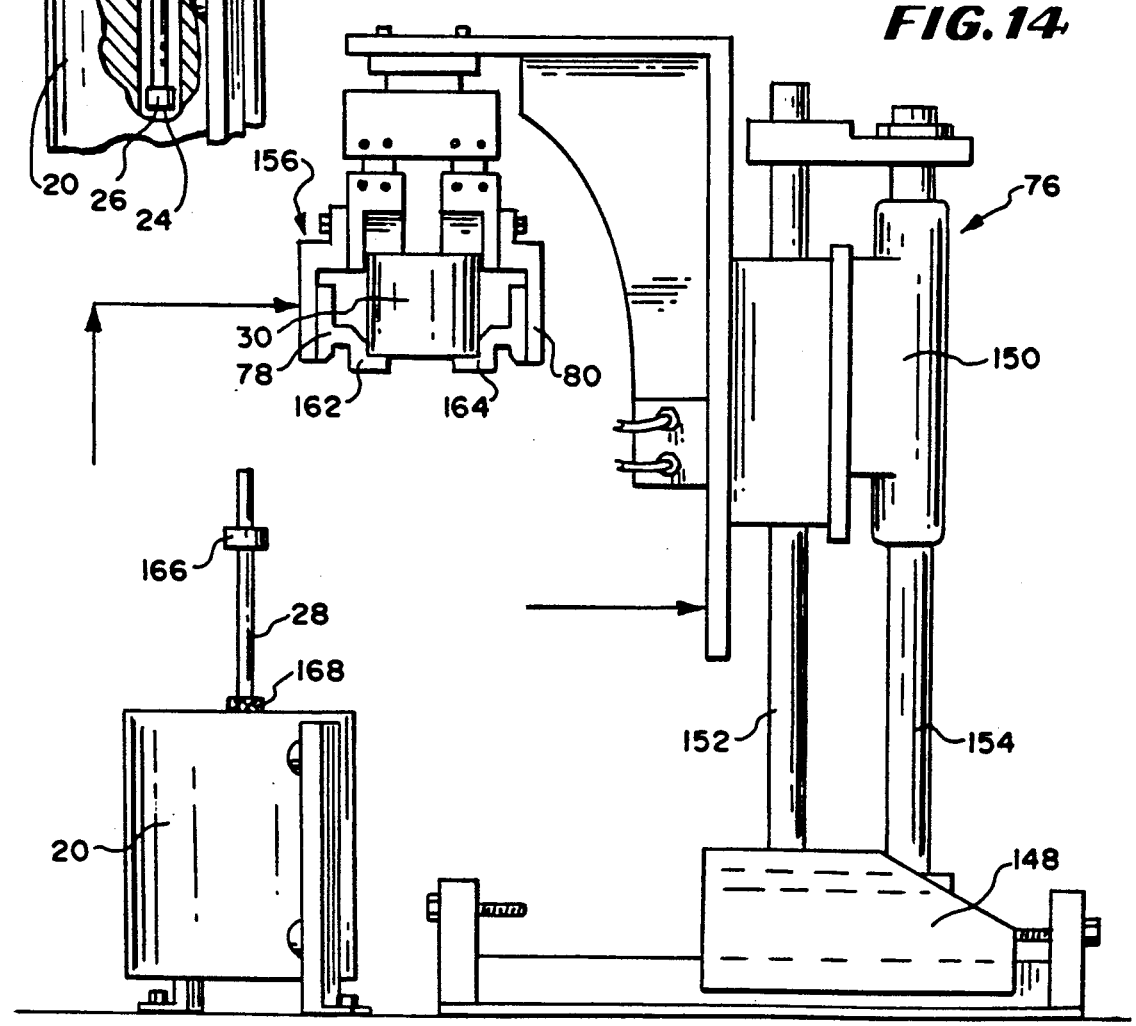
FIG. 14 is a side elevational view of the weight holding mechanism and shows the mechanism in its retracted position after it has lifted the weight off of the piston rod and has moved to its retracted position.
Figure 15:
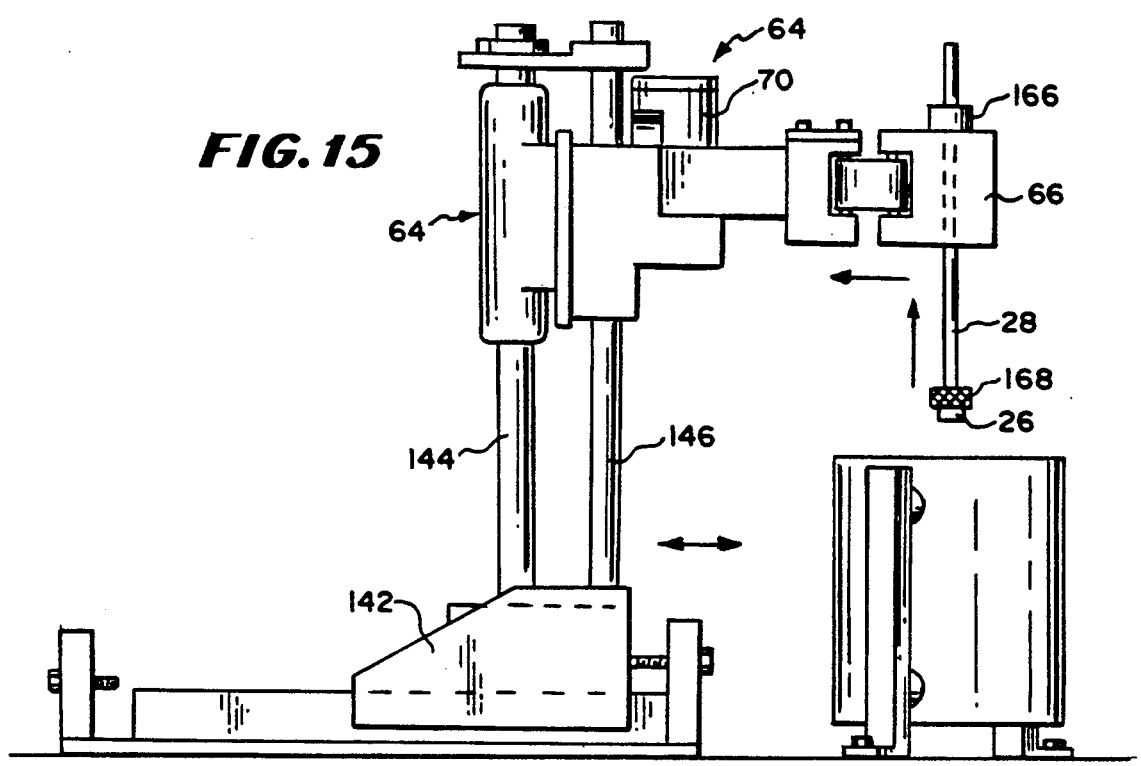
FIG. 15 is a side elevational view of the piston rod holding mechanism moved to a position to grasp the piston rod and remove same from the test cavity.

After the lever arm 170 has moved a certain arcuate distance under the force of the weight 30, it will contact the lower contact switch 176. When this contact switch 176 is engaged, the test period is ended and the vertically reciprocal carriage 150 is lowered to engage the weight 30 and pick it up and move it off of the piston rod 28 and upper collar 166 after which the horizontally reciprocal carriage 148 is operated to move the weight holding mechanism 76 back to its home position at station 6, as shown in FIGS. 13 and 14.

The time period, from the actuation of the upper contact switch 174 to the actuation of the lower contact switch 176 is supplied to the control circuit 138, as will be described in greater detail in connection with the description of FIG. 23.

In the meantime, under the control of the control circuitry 138 including a controller 180, the articulated mechanism 64 at the fourth station 4 is operated so that the horizontally movable carriage 142 is moved outwardly and the articulated mechanism 64 is moved downwardly with the jaws 66 and 68 in their open position. The jaws 66 and 68 are then rotated to grip the piston rod 28 below the upper collar 166, lift the piston rod 28 out of the test cavity 24 and subsequently retracted with the carriage 142 to the home position of the carriage 142 shown in FIG. 10.

Figure 16:
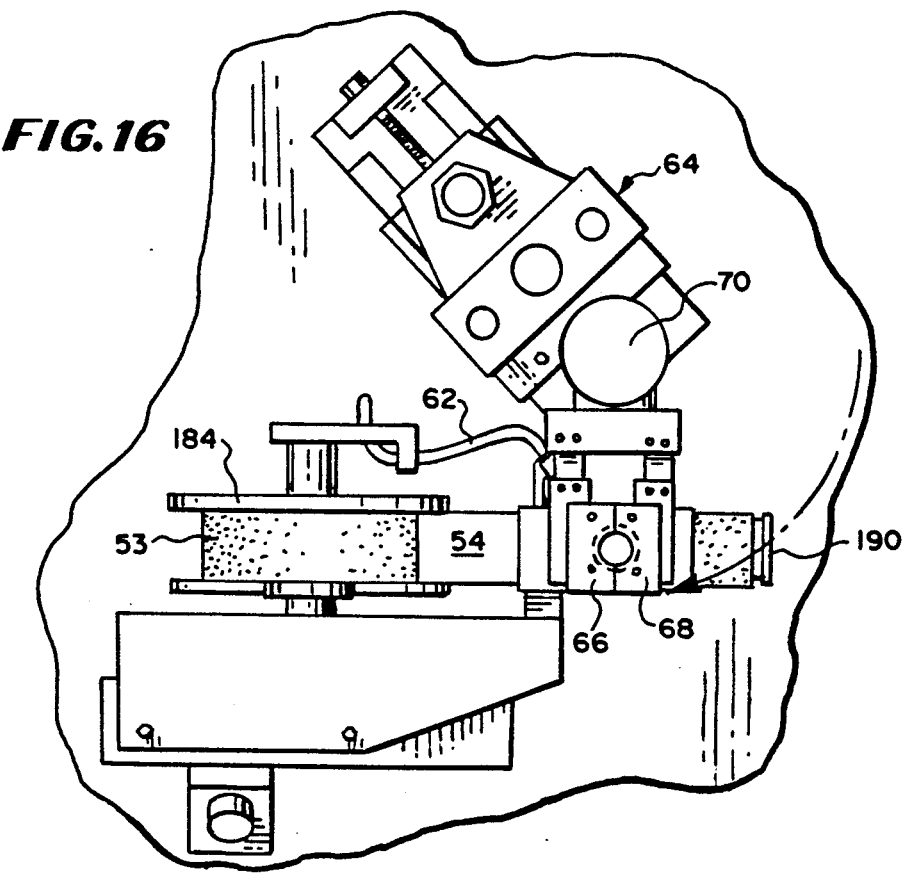
FIG. 16 is a top plan view of the piston rod holding mechanism at station 4 and a piston rod cleaning mechanism at station 3.
Figure 17:
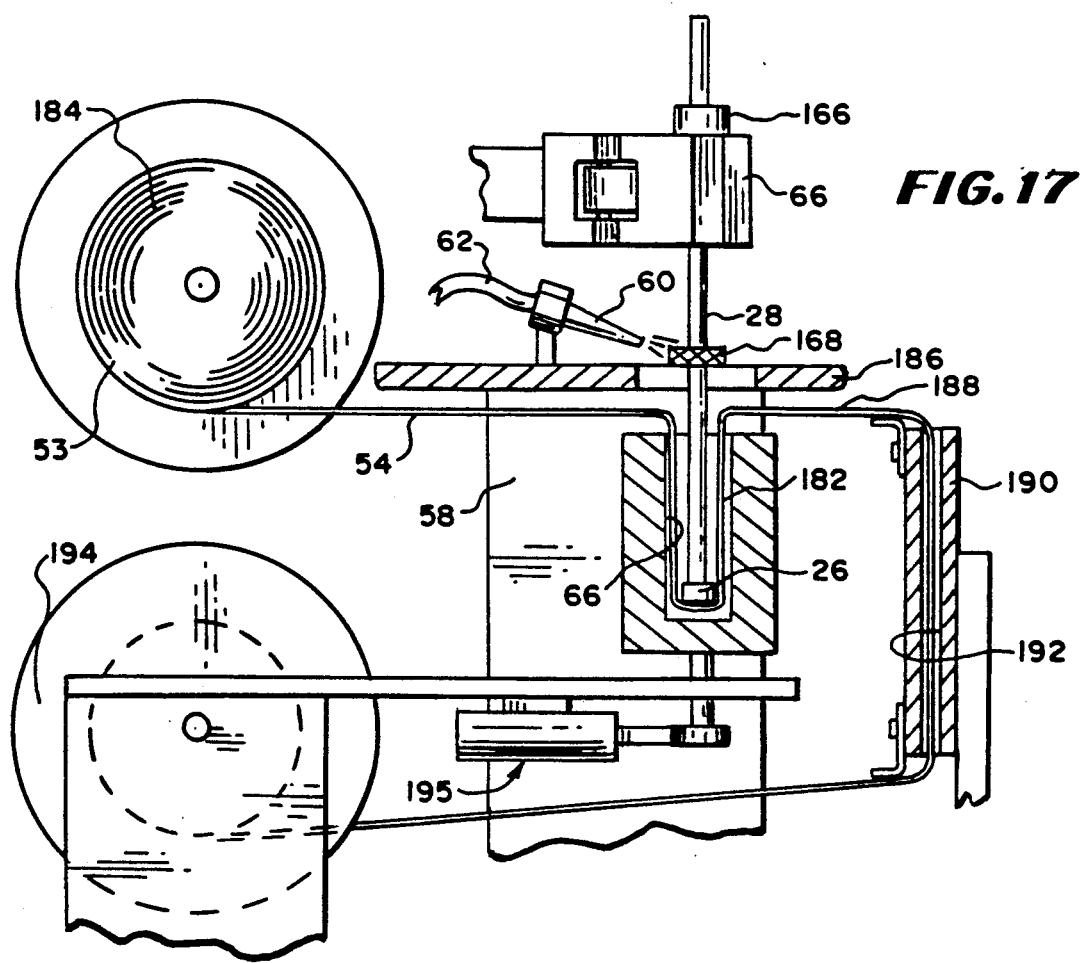
FIG. 17 is a fragmentary side elevational view of the piston rod cleaning mechanism at station 3 and shows a portion of the piston rod holding mechanism moved laterally to position the piston rod over a strip of cleaning material and shows the piston rod moved downwardly over the strip of cleaning material into a cleaning cavity.

Then, as best shown in FIG. 16, the jaws 66 and 68 are rotated together about a pivot axis of the pivoting mechanism 70 by the mechanism 70 to move the piston rod 28 over a section 182 of the strip 54 of cleaning material, such as cotton flannel material, which is typically gun cleaning cotton, located over the cleaning block 58 having the cleaning cavity 56 therein, as best shown in FIG. 17.

Referring now to FIG. 17, the vertically movable articulated mechanism 64 is now moved downwardly to push the piston foot 26 and piston rod 28 into the cleaning cavity 56 in the cleaning block 58 with the section 182 of the strip 54 of cleaning material. At the same time, an optional quantity of cleaning solvent is squirted onto the piston foot 26 and piston rod 28 and into the cleaning cavity 56 from the nozzle 60. As shown, station 3 includes the cleaning material supply reel 53 for mounting a roll 184 of the strip 54 of cleaning material, a guide plate 186 fixed above a path or flight 188 of the strip 54 of cleaning material over the cleaning block 58, a guide member 190 having a guide slot 192 therein through which the flight 188 of the strip 54 of cleaning material is trained to a pickup roller or reel 194. Preferably, the cleaning block 58 is rotated when the piston rod 28 is lowered into the cleaning cavity 56 with the section 182 of the strip 54 of cleaning material.

In the cleaning of the piston rod 28 at station 3, after each cleaning operation of the piston rod 28, the pickup roller 194 is indexed a certain amount to pull a new section 182 of the strip 54 of cleaning material into a position over the cleaning cavity 56 in the cleaning block 58. A mechanism 195 is provided for rotating the cleaning block 58.

Figure 18:
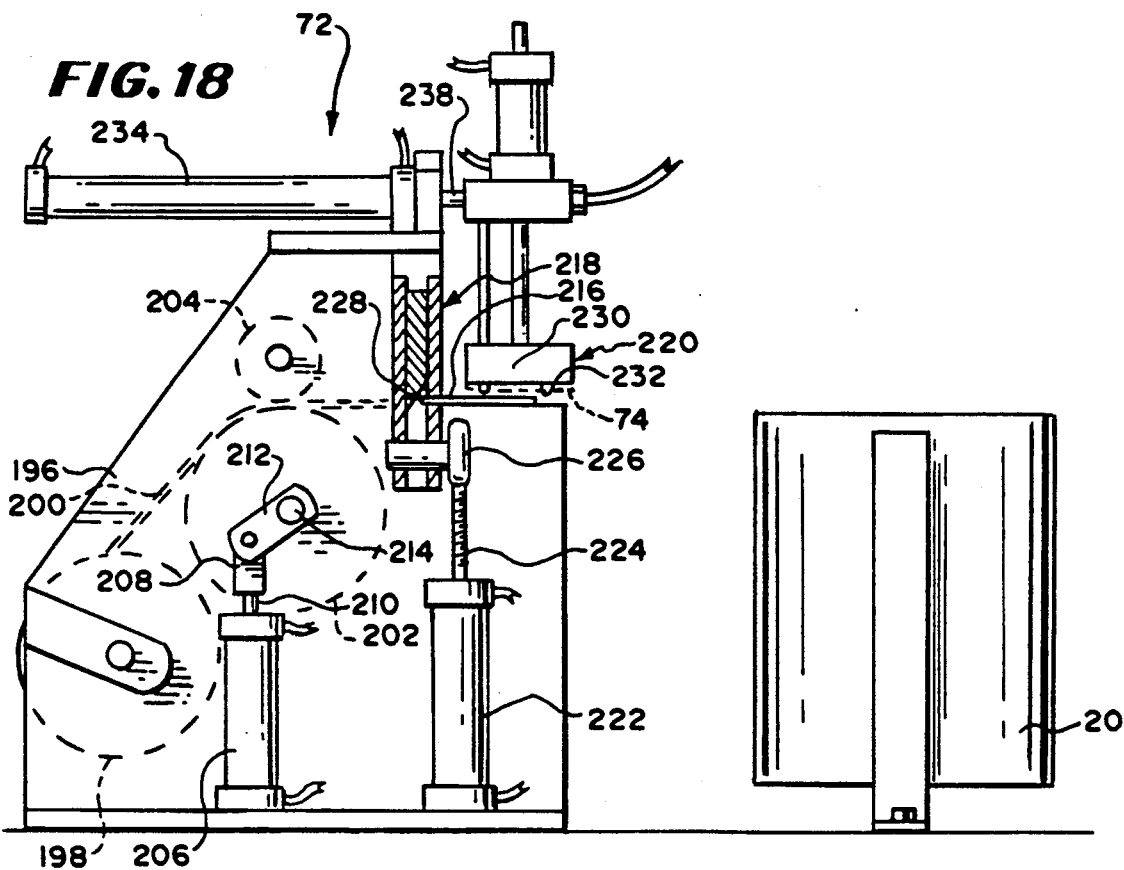
FIG. 18 is a side elevational view of a cotton applicator mechanism at station 5 where a suction device of the applicator mechanism picks up a cut piece of cotton or cotton patch.

In the meantime, referring to FIG. 18, a test barrel cleaning operation is commenced starting at station 5 where there is located the cotton applicator mechanism 72. The cotton applicator mechanism 72 includes a framework 196 mounting a supply reel 198 of a strip 200 of cleaning material, such as cotton flannel material used for cleaning gun barrels. The strip 200 of cleaning material is trained over an indexing wheel 202 and between the indexing wheel 202 and an idler roller 204. The idler roller 204 is made of an elastomeric material and is mounted on the framework 196 in a position to abut against or engage the indexing wheel 202 so that the strip 200 of cleaning material fed between them is tightly gripped by the interaction between the idler roller 204 and the indexing wheel 202.

A cylinder 206 is fixed on the framework 196 and a distal end 208 of a piston rod 210 extends from the cylinder 206 and engages a ratchet type cam arm 212 extending radially from a shaft 214 on which the indexing wheel 202 is mounted. Operation of the cylinder 206 causes the piston rod 210 to move upwardly moving the cam arm 212 to rotate or index the indexing wheel 202 to advance a section 216 of the strip 200 of cleaning material forwardly to the right and beneath a shearing mechanism 218 and a suction mechanism 220.

The shearing mechanism 218 includes a pneumatic cylinder 222 having a piston rod 224 extending therefrom. A distal end 226 of the piston rod 224 is connected to the shearing mechanism 218 and is operable to move a shearing blade 228 of the shearing mechanism 218 downwardly to cut the section 216 of the strip 200 of cleaning material which then becomes cleaning material patch 74.

Figure 19:
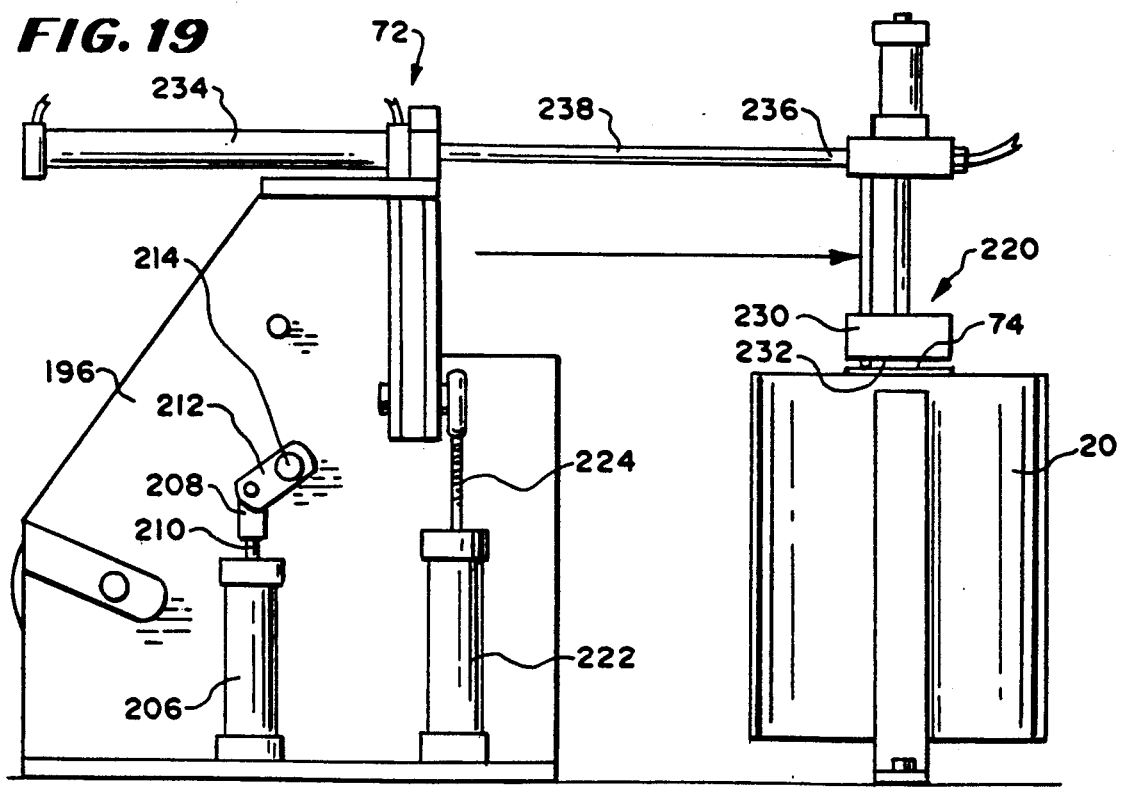
FIG. 19 is a side elevational view of the cotton applicator mechanism shown in FIG. 18 but with the suction mechanism extended to place the cotton patch over the test cavity in the heating block.

The suction mechanism 220 includes a platen 230 having a lower surface 232. At least one suction opening (not shown) opens onto the surface 232. Once the cleaning material patch 74 has been cut, the suction mechanism 220 is operated to pull the cleaning material patch 74 against the lower surface 232 of the platen 230. Then a cylinder 234 is actuated to advance the suction mechanism 220 mounted to the distal end 236 of a piston rod 238 extending from the cylinder 234 forwardly over the heating block 20, as shown in FIG. 19. Here the application of suction is stopped and a short burst of gas such as air or nitrogen is supplied to the lower surface 232 of the platen 230 to position the cleaning material patch 74 on the heating block 20 over the test cavity 24 in the heating barrel 20.

Figure 21:
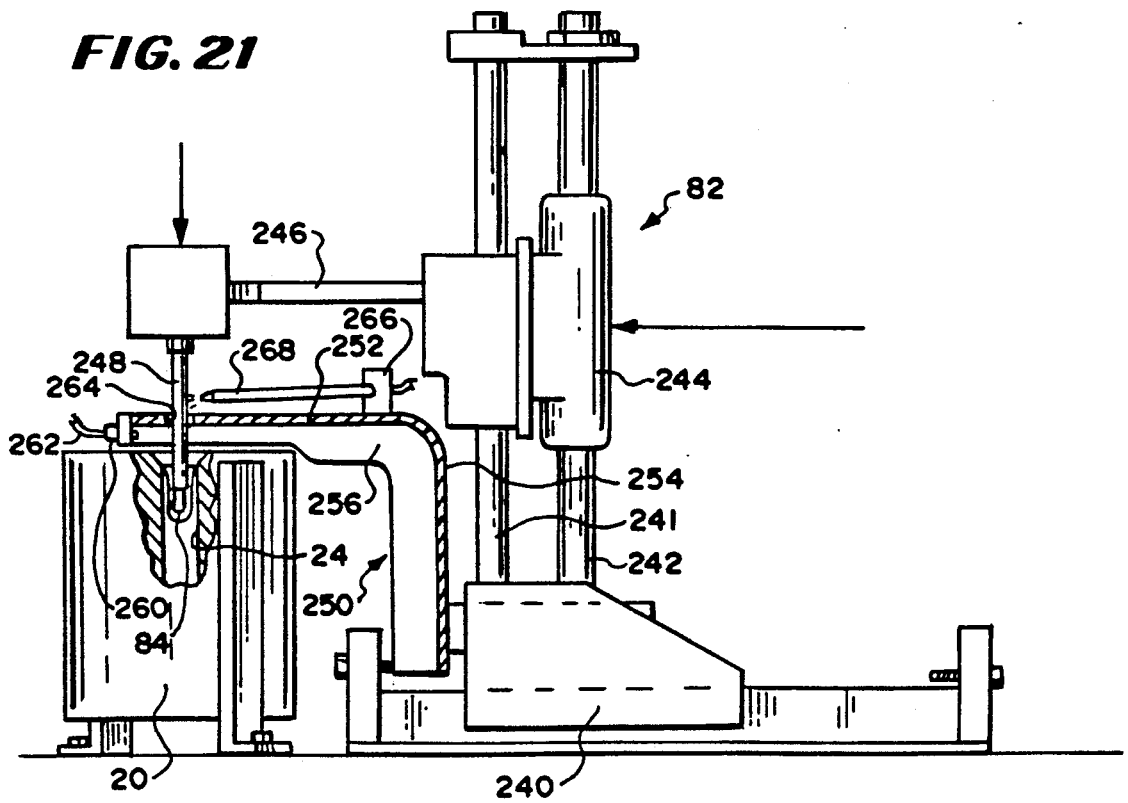
FIG. 21 is a side elevational view of the cavity cleaning mechanism shown in FIG. 20 in its extended position and shows a cleaning rod of the cavity cleaning mechanism lowered to move the cotton patch into the test cavity in the heating block.

Now the cavity cleaning mechanism 82 located at station 7 is operated. As shown in FIGS. 20 and 21, the cavity cleaning mechanism 82 includes a lower horizontally reciprocal carriage 240 mounting at least two guide rods 241 and 242 on which are slidably mounted a vertically reciprocal carriage 244. An arm 246 extends outwardly from the vertically reciprocal carriage 244 and has a cleaning rod 248 depending therefrom.

Also, mounted to the horizontally reciprocal carriage 240 is a L-in-cross-section chute 250 which as a top wall 252, a back wall 254 and an L-shaped side wall 256 on at least one side thereof, as shown in FIGS. 20 and 21. The chute 252 also has a short front wall 258 depending from the front end of the top wall 252. The front wall 258 has mounted therein a gas nozzle 260 to which in connected a gas hose 262 for delivery of the gas.

The top wall 252 is provided with a hole 264 therethrough beneath the depending cleaning rod 248, as shown.

In the operation of the cavity cleaning mechanism 82, the horizontally reciprocal carriage 240 is actuated to move same from a home position to a forward extended position where the depending rod 248 is positioned over the test cavity 24 in the heating block 20. Then the vertically reciprocal carriage 244 is actuated to move the cleaning rod 248 downwardly through the hole 264 in the top wall 252 of the chute 250 and then into the test cavity 24 and, as it so moves, it pushes the cleaning material patch 74 into the test cavity 24 for cleaning same.

Mounted on the top wall 252 of the chute 250 is a bracket 266 from which a tube 268 extends to a nozzle 270 positioned above the hole 264 in the top wall 252. A hose 272 is connected to the tube 268 for supplying cleaning solvent through the nozzle 270 to the cleaning rod 248 and to the cleaning material patch 74.

Figure 22:
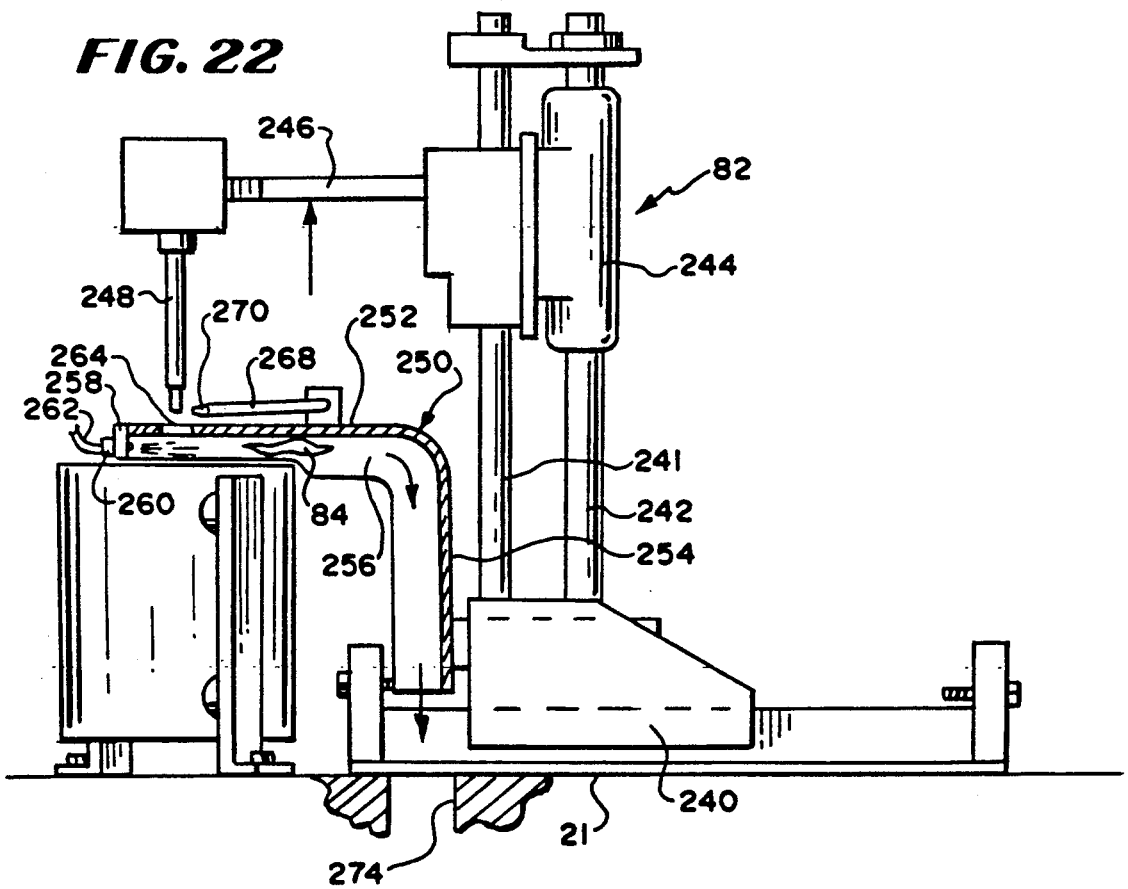
FIG. 22 is a side elevational view of the cleaning mechanism shown in FIG. 20 with the cleaning rod raised to an upper position and shows a jet of air actuated to blow the used cotton patch that had been used to clean the test cavity in the heating barrel radially outwardly and downwardly through a discharge chute.

As shown in FIG. 21, after the horizontally reciprocal carriage 240 is moved forwardly, the vertically reciprocal carriage 244 is moved downwardly to move the cleaning rod 248 downwardly. At the same time, optional cleaning solvent is squirted from the nozzle 270 onto the cleaning rod 248 and onto the cleaning material patch 74 and the cleaning rod 248 moves downwardly to clean the test cavity 24 in the heating block 20 after which it is retracted upwardly as shown in FIG. 22. The cleaning material 74, now used cleaning material patch 84, is carried with the cleaning rod 248 upwardly to the area of the chute 250 above the test cavity 24. Then a burst of the gas is provided from the nozzle 260 mounted in the front wall 258 of the chute 250 to blow the used cleaning material patch 84 rearwardly along the vertical back wall 254 of the chute 250 and downwardly through an opening 274 (FIG. 22) in the table 21 on which the machine 10 is mounted into a refuse collecting receptacle (not shown) which collects the used cleaning material patch 84.

A burst of the gas is also supplied from a nozzle 276 at the end of a gas line 278 which extends from station 2 to a position on the heating block 20 as shown in FIGS. 1 and 2, to assist in blowing the used cleaning material patch 84 into the chute 250.

Figure 23:
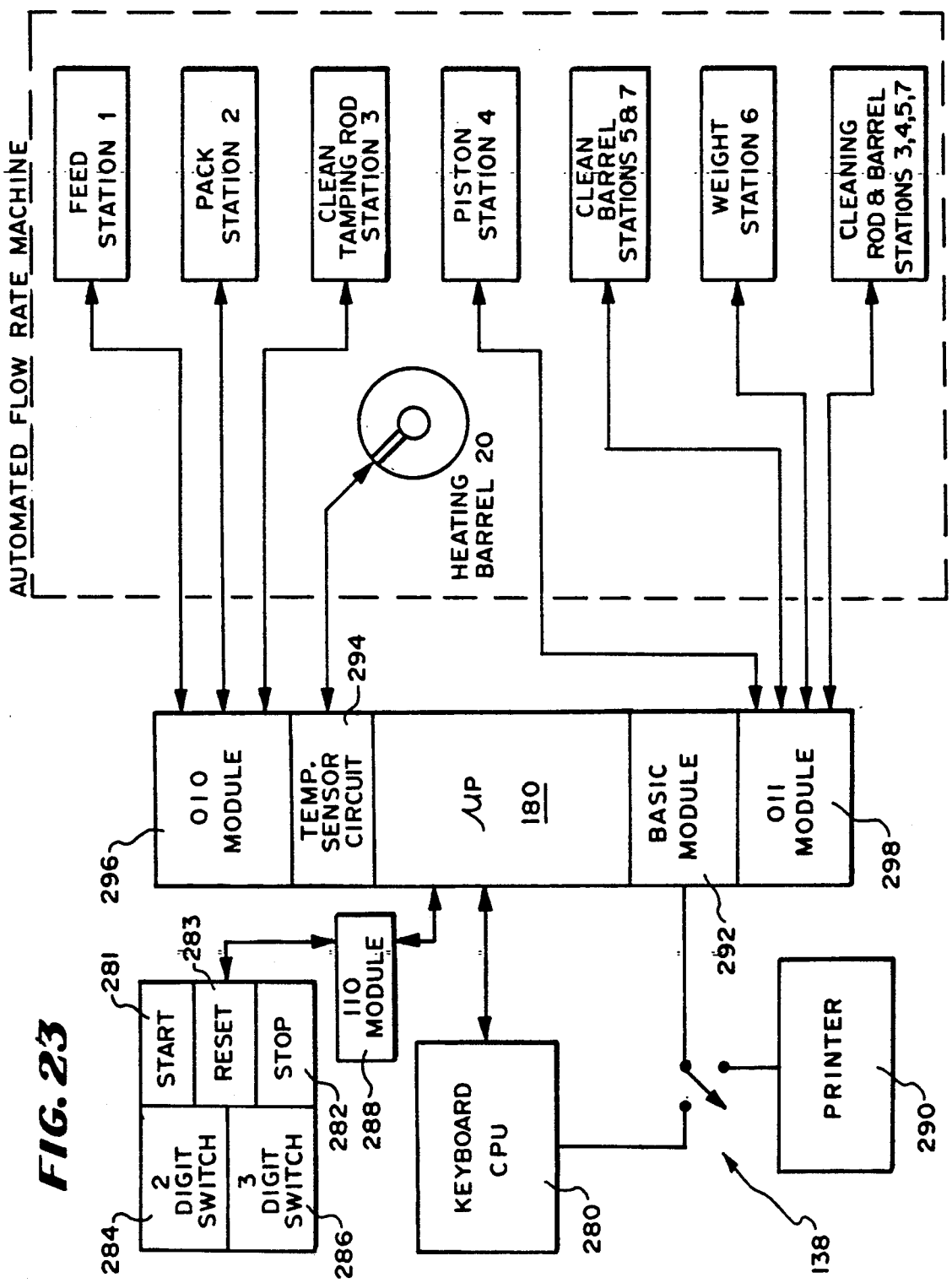
FIG. 23 is a block schematic diagram of the electrical control circuit for the automated flow rate machine.
Figure 24A:
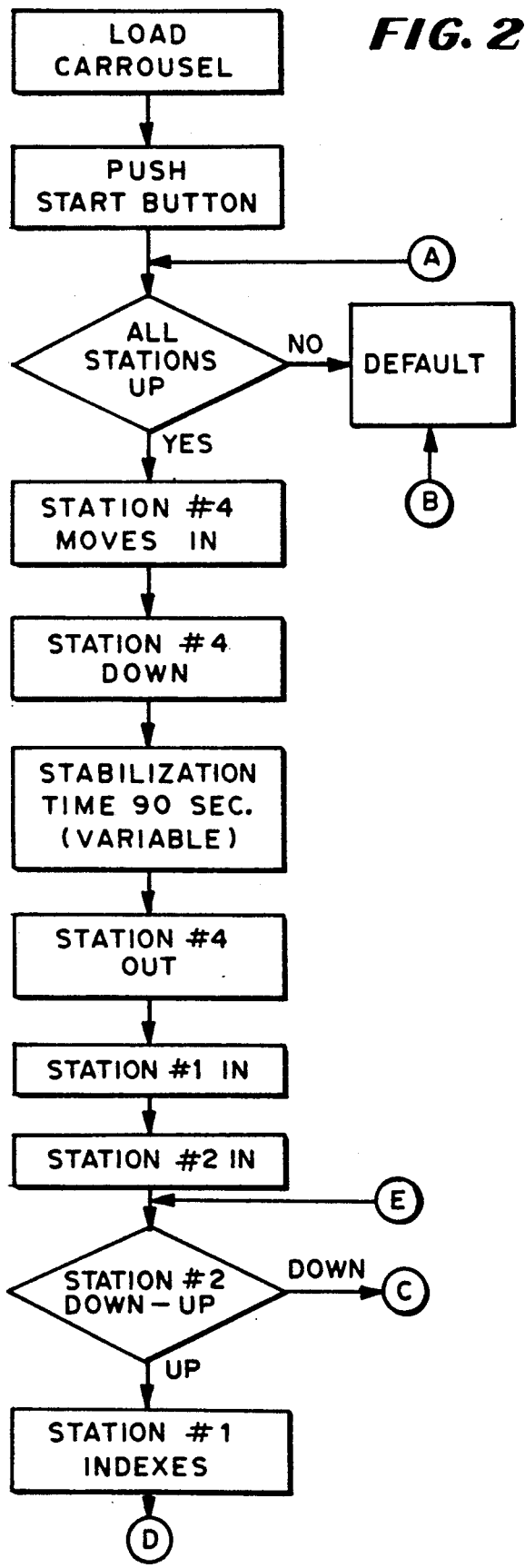
FIGS. 24A-24D comprise a flow chart of the steps carried out by the control circuit shown in FIG. 23 for operating the mechanisms at the seven stations for carrying out one automated flow rate evaluation.
Figure 24B:
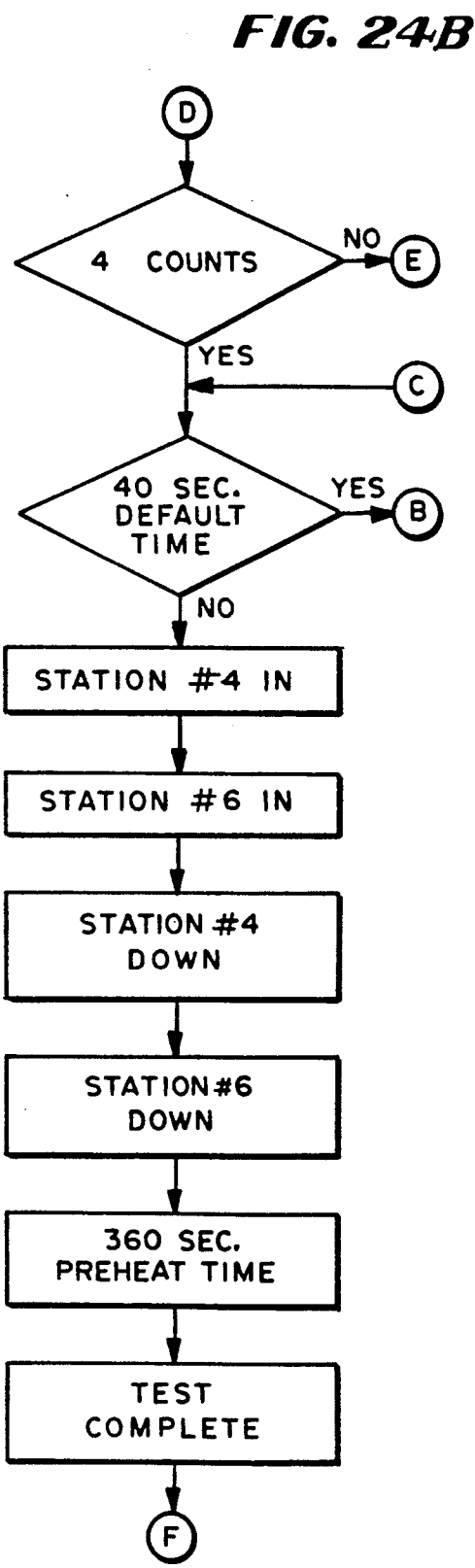
Figure 24C:
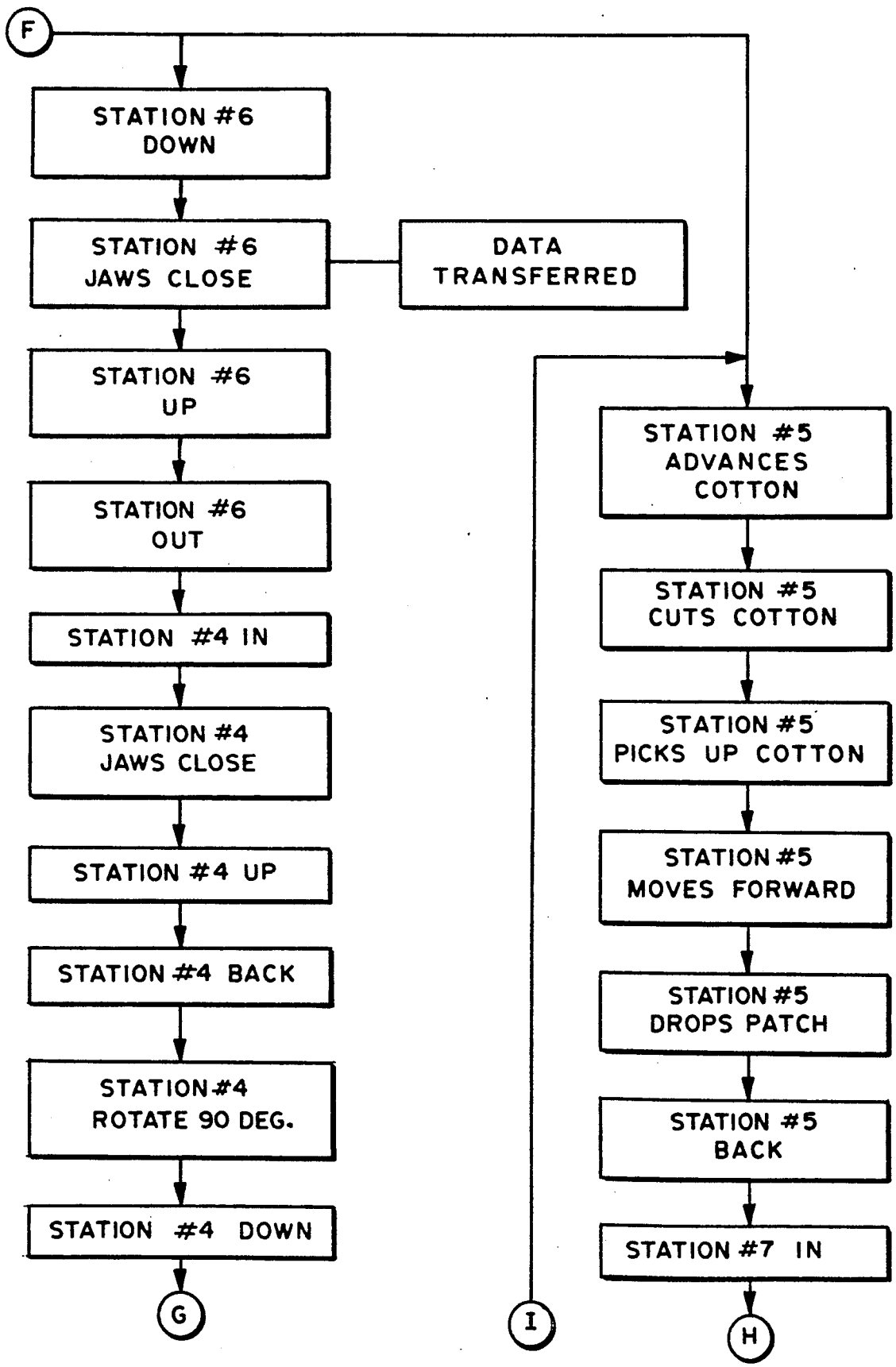
Figure 24D:
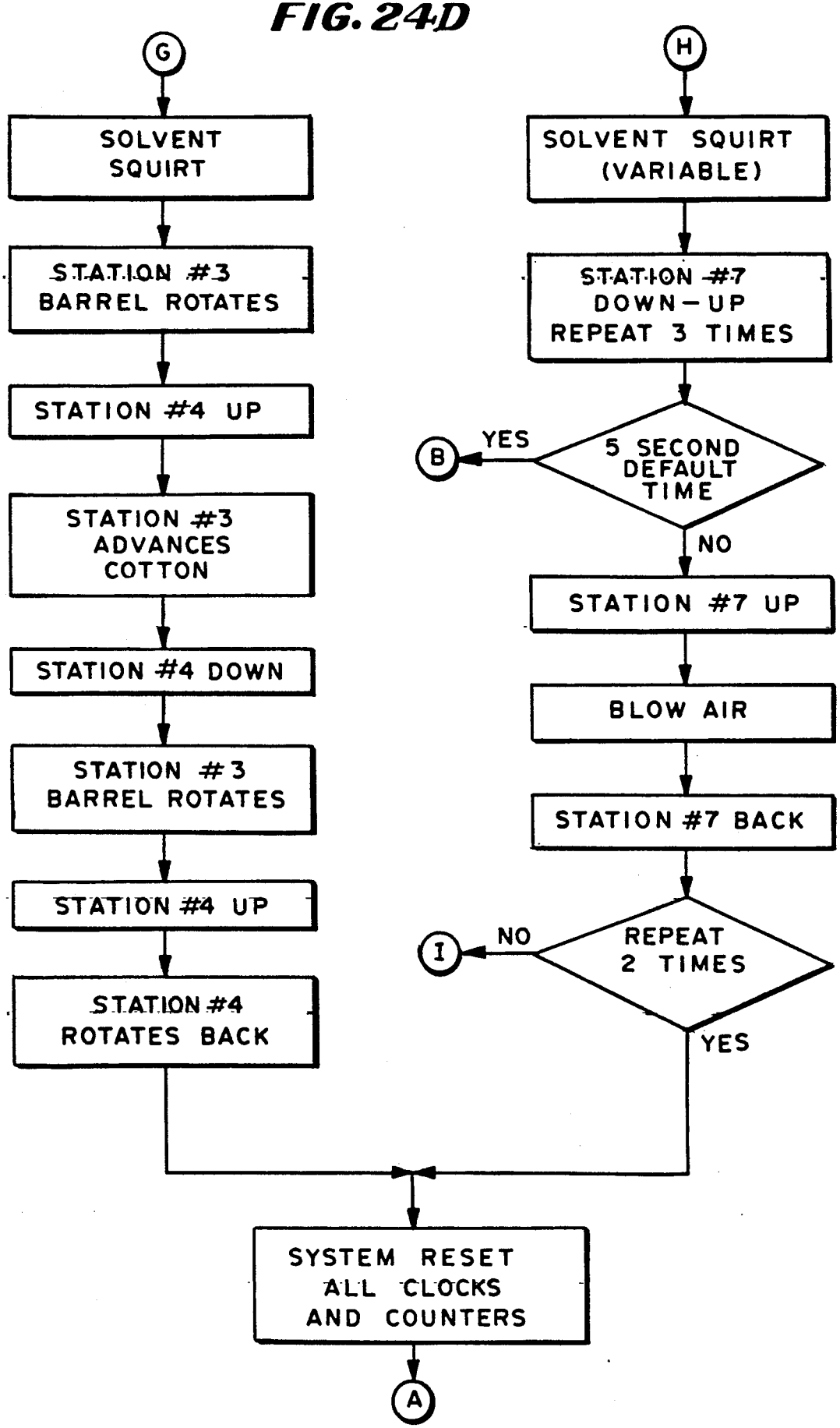

In FIG. 23, there is shown a simplified block circuit diagram of a control circuit 138 for the automated flow rate machine 10. The control circuit 138 includes the microprocessor-controller 180 which is typically an Allen-Bradley microprocessor with controller. Coupled to the microprocessor-controller 180 is a keyboard 280. START, STOP and RESET buttons 281, 282, and 283 as well as digit switches 284, 286 are coupled through an interface module 288 to the microprocessor-controller 180. A printer 290 can be coupled through a basic module 292 (operating on basic language) to the microprocessor-controller 180. A temperature sensor circuit 294 is coupled to the microprocessor-controller 180 and to a temperature sensor on the heating block 20 for controlling the heating of the heating barrel 20 relative to the sensed temperature of the heating barrel 20.

Stations 1–3 are coupled through an interface module 296 to the microprocessor-controller 180. Likewise, stations 4–7 are coupled through an interface module 298 to the microprocessor 180.

Operating programs are mounted in the programmable microprocessor-controller 180 for initiating, monitoring and controlling the various operations described above and below at the seven stations 1–7 described above.

The flow chart in FIGS. 24A–24D defines the steps of operation of the machine 10 in terms of movement of a station although it is to be understood that it is mechanisms at the stations that are moved inwardly or outwardly and in some instances, up or down. The legends for each of the steps are self-explanatory and use the convention of station numbers for describing the sequence of steps carried out by the mechanisms at the different stations 1–7 of the machine 10 in carrying out one complete test and cleaning of the tamping rod 48, the piston foot 26, the piston rod 28 and the test cavity 24.

The sequence of operations or steps of the process carried out by the machine 10 can be defined as follows:

STEP 1

The articulated mechanism 64 at station 4 moves outwardly and downwardly to place the piston rod 28 in the test cavity 24 in the heating block 20 for a stabilization period, which is a stabilization/preheating time of from 0 to 15 minutes, typically one and half minutes, or 90 seconds. Then, after the stabilization period, the piston rod 28 is moved up and out of the heating block 20 and back to the home position of the horizontally reciprocal carriage 128 at station 4.

STEP 2

The carousel mounting carriage 42 at station 1 is moved inwardly to position the sample receiving cavity 50 in line with the test cavity 24.

STEP 3

The carousel 22 is tapped by a tapping mechanism 300 (FIG. 6) and indexed to place the first of a sequence of four sample receiving cavities 50 in line with the test cavity 24 in the heating block 20.

STEP 4

The horizontal carriage 128 is moved from its home position at station 2 to its extended position and the tamping mechanism 46 is then actuated to move the tamping rod 48 down and up to push the polymer material from the sample receiving cavity 50 into the test cavity 24.

Steps 3 and 4 are repeated four times.

STEP 5

The carriage 42 at station 1 is moved back to its home position and the carriage 128 at station 2 is moved back to its home position.

STEP 6

The carriage 142 at station 4 moves in and down to move the piston rod 28 into the heating block 20 as shown in FIG. 9.

STEP 7

The weight holding mechanism 76 at station 6 is moved inwardly and down with the weight 30.

STEP 8A

A heating time of 6 to 8 minutes allows the piston foot 26 and sample in the test cavity 24 to be heated to a desired temperature. At this time, the articulated mechanism 64 at station 4 is holding the piston rod 28 thereby to hold the piston rod 28 and weight 30 in place.

STEP 8B

If the weight 30 does not free fall, the jaws 78 and 80 will position the weight 30 one half inch above the actuating switch arm 170 with the weight holding mechanism 76. There are two situations that can occur:

In Situation 1, the weight 30 free falls past the switch arm 170 after STEP 9 through STEP 10 and the weight 30 continues to fall until the second contact switch 176 is actuated thereby to complete a test stage.

In Situation 2, the weight 30 doesn't free fall. The weight holding mechanism 76 pushes the weight 30 downwardly to one half inch above the switch arm 170 and releases the weight 30 at STEP 9. Then the test begins when the switch arm 170 is engaged at STEP 10.

STEP 9

Here the jaws 66 and 68 of the articulated mechanism 64 at station 4 move outwardly and downwardly out of the path of the piston rod 28.

STEP 10

The weight holding mechanism 76 at station 6 is still in its extended position and the weighted piston foot 26 now will fall or be forced down. The weight 30 normally moves down in a free fall against the actuating arm 170 which initiates the timing period by actuating the upper contact switch 174 and will continue moving until the second contact switch 176 is actuated.

STEP 11

After the second switch actuation (closing of the second switch 176 or actuation of a second sensor), the time period is sent to the microprocessor-controller 180. The weight engaging jaws 78 and 80 moves downwardly to the top of the heating block 20, pick up weight 30 and lift it up and then moves away from the heating block 20.

Steps 12-17 will now be described and it is to be understood that Steps 18-22 take place at the same time as Steps 12-17. This is shown in the program in FIGS. 24C and 24D.

STEP 12

At this Step 12, the carriage 142 at station 4 moves inwardly from its home position and lifts the piston rod 28 out of the test cavity 24, moves back to its home position and then rotates 90 degrees to the right over station 3, as shown in FIG. 16.

STEP 13

The piston rod holding mechanism 64 moves down into station 3 pushing the piston foot 26 and the section 182 of cotton into the cleaning cavity 56. Two counts or squirts of cleaning solvent, such as decahydronaphthalene a solvent for thermoplastics such as polystyrene, polyethylenes and polypropylene, are squirted onto the piston rod 28.

STEP 14

The cleaning block 58 at station 3 is rotated around the section 182 of cleaning material and the piston rod 28 and piston foot 26.

STEP 15

The articulated piston rod holding mechanism 64 at station 4 moves upwardly to lift the piston rod 28 out of the cleaning block 58. An indexing switch (not shown) allows the pickup roller 194 to advance two counts to advance a new section 182 of cleaning material at station 3 over the cleaning block 58.

STEP 16

The articulated mechanism 64 moves the piston rod 28 down again over the section 182 of cleaning material and into the cleaning cavity 56 in the cleaning block 58 and the cleaning block 58 is rotated.

STEP 17

Steps 15 and 16 are repeated.

STEP 18

At station 5 the indexing wheel 202 is operated to advance the cleaning material strip 200. The shearing mechanism 218 is operated to cut the cleaning material patch 74. Then the suction head 220 at station 5 goes down over the cleaning material patch 74, picks it up and the suction head 220 is moved over the test cavity 24 and a puff of gas is ejected from the suction head 220 to drop the cleaning material patch 74 onto the top of the heating block 20. Then the suction head 220 is withdrawn.

STEP 19

The barrel cleaning mechanism 82 at station 7 is moved in over the heating block 20 and two counts or squirts of cleaning solvent are ejected from the nozzle 270 onto the cleaning material patch 74. Then the cleaning rod 248 is moved downwardly and upwardly four times.

STEP 20

A burst of gas from the gas line 262 then blows the used cleaning material patch 84 off of the top of the barrel 20 and a burst of gas from the gas line 278 extending from station 2 assists in blowing the used cleaning cloth patch into the chute 250.

STEP 21

The barrel cleaning mechanism 82 is retracted to its home position at station 7.

STEP 22

Steps 18-21 are repeated two times.

It is to be understood that from 1 to up to 4 sample receiving cavities 50 can be utilized from one sample batch. The contents of four sample cavities is preferred for a batch.

The cleaning material is typically the type used for cleaning gun barrels, which is a double knapped flannel cotton.

The gas pressure utilized is up to 100 psi and 85 psi is preferred. Although nitrogen or air can be used as the gas, air is preferred because of its lower cost.

Figure 25:
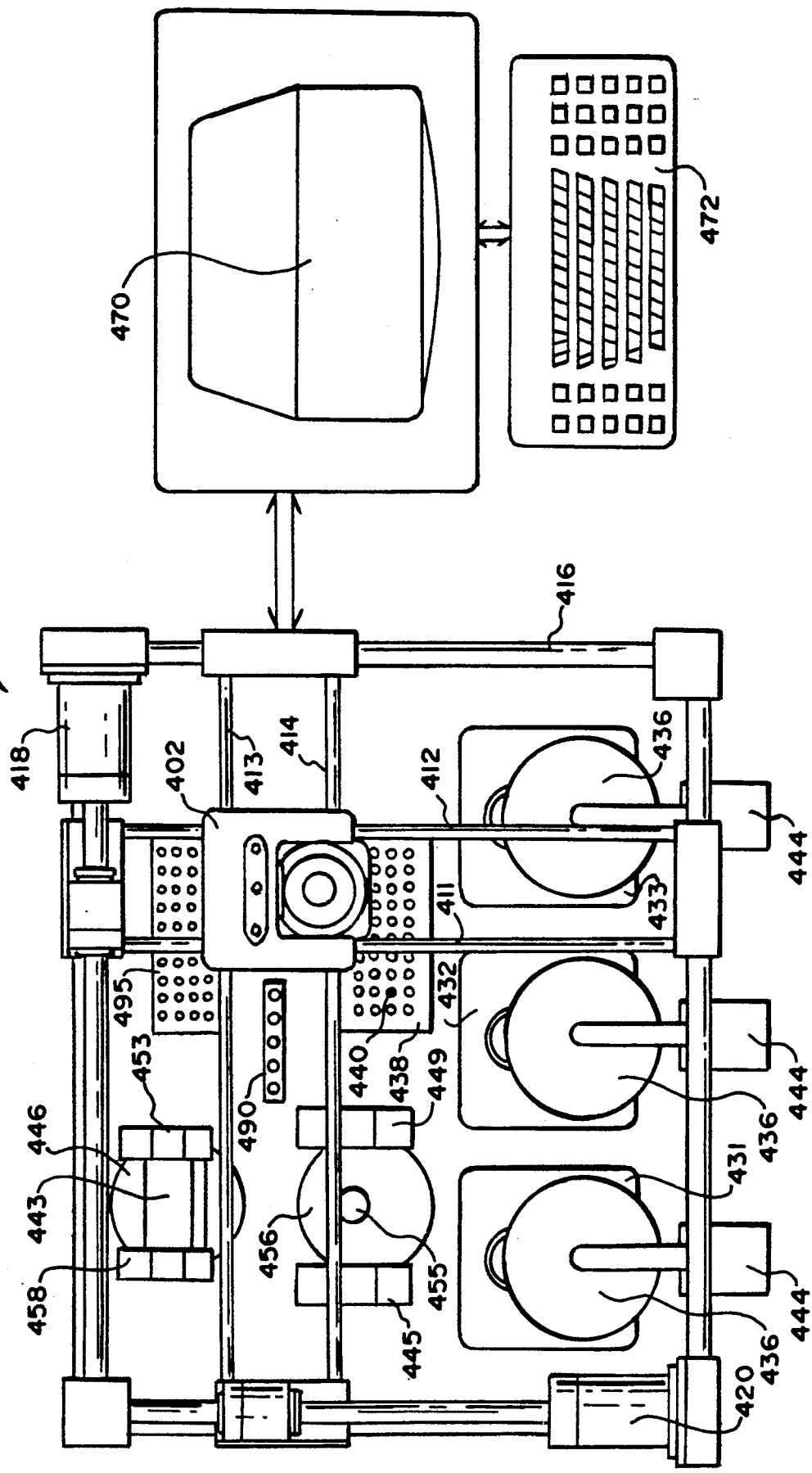
FIG. 25 is a top plan view of another embodiment of the automated flow rate machine of the present invention which includes a cartesian movable overhead manipulator positioned over several heating blocks or test stations, a sample pickup station, a sleeve/die insert cleaning station and a piston rod cleaning station.
Figure 29:
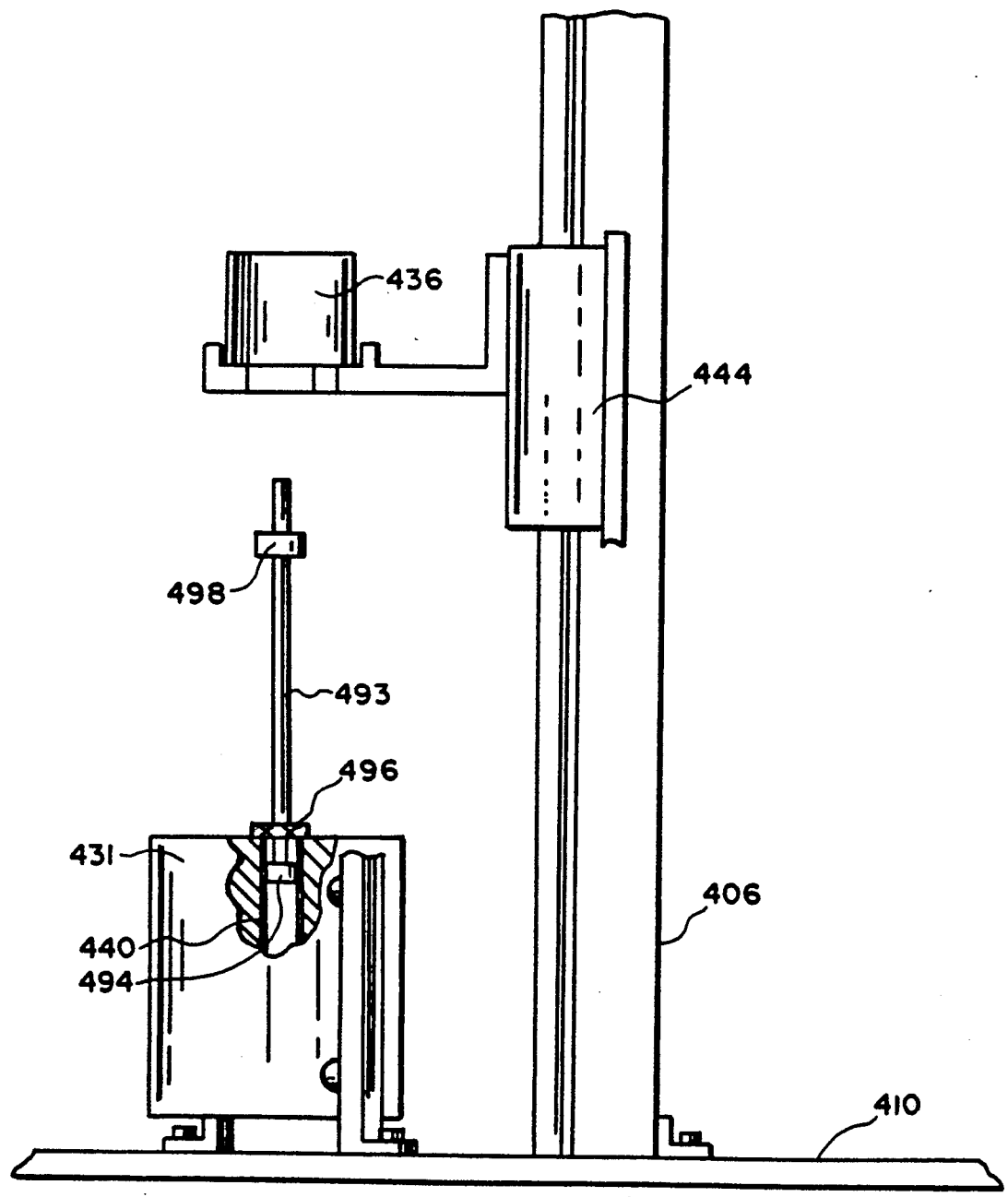
FIG. 29 is a side elevational view of the heating block of the embodiment shown in FIG. 25.

Another embodiment of the apparatus of the present invention is an automated flow rate machine 400 shown in FIG. 25 which includes a cartesian overhead manipulator 402 that is movable in a X-axis direction or a Y-axis direction on sliding bars 411-414 mounted on a framework 416 which is mounted on a table 410 (FIG. 29). A motor 418 moves the manipulator 402 on the Y-axis a motor 420 moves the manipulator 402 on the X-axis. The machine 400 has three heating blocks or chambers 431, 432 and 433 which define test stations Nos. 1, 2 and 3, respectively. Each heating block 431, 432 and 433 has a movable weight 436 (FIG. 29) that is moved vertically of the heating blocks 431, 432 and 433.

A sample sleeve rack 438 is positioned in the machine 400 and has multiple sleeve/die inserts 440 mounted therein. The number of sleeve/die inserts can be 40 or more. Each one of the sleeve/die inserts 440 has a die 442 (FIG. 26) in the bottom of the sleeve/die insert 440 so that the internal surface of each sleeve/die insert 440 also defines a test cavity. A collection rack 495 is positioned in the machine 400 to receive multiple sleeve/die inserts 440 which have been used for tests and subsequently cleaned. A piston preheat station 490 is positioned in the machine 400 to house clean piston rods 493 (FIG. 29) that are maintained at the flow rate test temperature to accelerate the testing process.

The overhead manipulator 402 is operated to pick up the sleeve/die insert 440 which has a polymer sample in it and positions the sleeve/die insert in one of the heating barrels 431, 432 and 433. Initially the test sleeve/die insert 440 is placed in any one of the heating blocks 431, 432 and 433, whichever heating block is available for a test. Typically, the heating block 431, test station No. 1, would be the first heating block to be used. The machine 400 by means of the manipulator 402 positions the sleeve/die insert 440 in the heating block 431 followed by the positioning of a piston rod 493 (FIG. 29) in the sleeve/die insert 440 so that the sleeve/die insert 440 and the piston rod 493 can be heated to the desired test temperature. A test weight 436 is lowered onto the piston rod 493 with the test weight 436 held in position on the piston rod 493 on an upper collar 498 while a lower collar 496 slidably located on the piston rod 493 rests on the heating block 431, 432 or 433.

After a period of sufficient duration to heat to the desired temperature the sleeve/die insert 440 and the contents thereof are heated as well as the piston rod 493, the test weight 436 is allowed to fall. As the test weight 436 falls, it will trigger a noncontact switch (not shown) to indicate that the test has started and when the test weight 436 has gone down a predetermined distance, it will actuate a second noncontact switch (not shown) to indicate that the test is completed. As in machine 10 the extruded polymer of the flow rate test is collected in an appropriate container and disposed of in an appropriate manner including recycling of the polymer.

The switches can be noncontact switches, such as an infrared LED switch, or the switches can be contact switches. Once the test weight 436 triggers the lower switch, the time is taken or captured and related to grams per 10 minutes utilizing the microprocessor or computer 470. The flow rate can then be used as an indication of the molecular weight or other parameters of the thermoplastic polymer.

Figure 30:
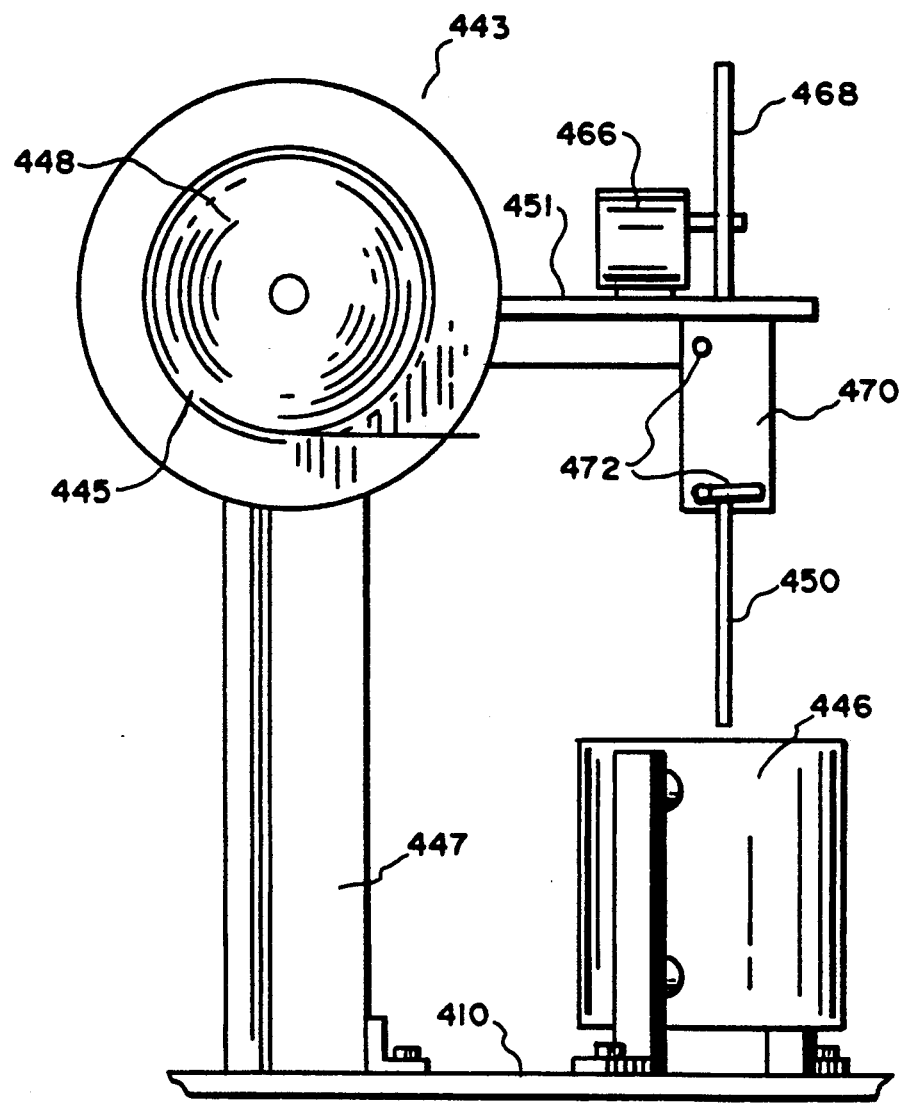
FIG. 30 is a side elevational view of the sleeve/die insert cleaning station embodiment shown in FIG. 25.

Once the flow rate test is completed, a mechanism 444 (FIG. 29), operated by a motor (not shown) and slidably mounted to test support stand 406 which in turn is mounted on the table 410 of the machine 400, at each heating block 431, 432 and 433 will lift the test weight 436 upward. Then the manipulator 402 is operated to retrieve the sleeve/die insert 440 and move the sleeve/die insert 440 to a cleaning block 446 (FIG. 30).

The cleaning block 446 has a support stand 447 mounted to the table 410 which has fixed to, and extending outwardly from the upper end of the support stand 447, a horizontal support 451. At the distal end of horizontal support 451 is located an opening for locating a rack and pinion vertical drive 468 which is driven by a motor 466. A cleaning rod 450 is fixed to the distal end of the vertical drive 468. A rod guide and roller mount 470 is attached to the underside of the horizontal support 451 and is positioned to receive the vertical drive 468. The rod guide and roller mount 470 has several guide rollers 472 for guiding the cleaning material received from a cleaning material source roller 445 over the cleaning block 446 to a take up roller 449. The cleaning block 446 is located below the vertical drive 468 and a cleaning cavity (not shown) in the cleaning block 446 is aligned to receive the cleaning rod 450. A sleeve/die insert cleaning material strip 448 from the source roller 445 will move simultaneously with cleaning rod 450 while the cleaning block 446 remains stationary. The take up roller 449 is operated to move a clean section of the strip 448 over the cleaning cavity in the cleaning block 446. At the completion of the cleaning cycle the manipulator 402 transports the sleeve/die insert 440 to the collection rack 495.

Figure 31:
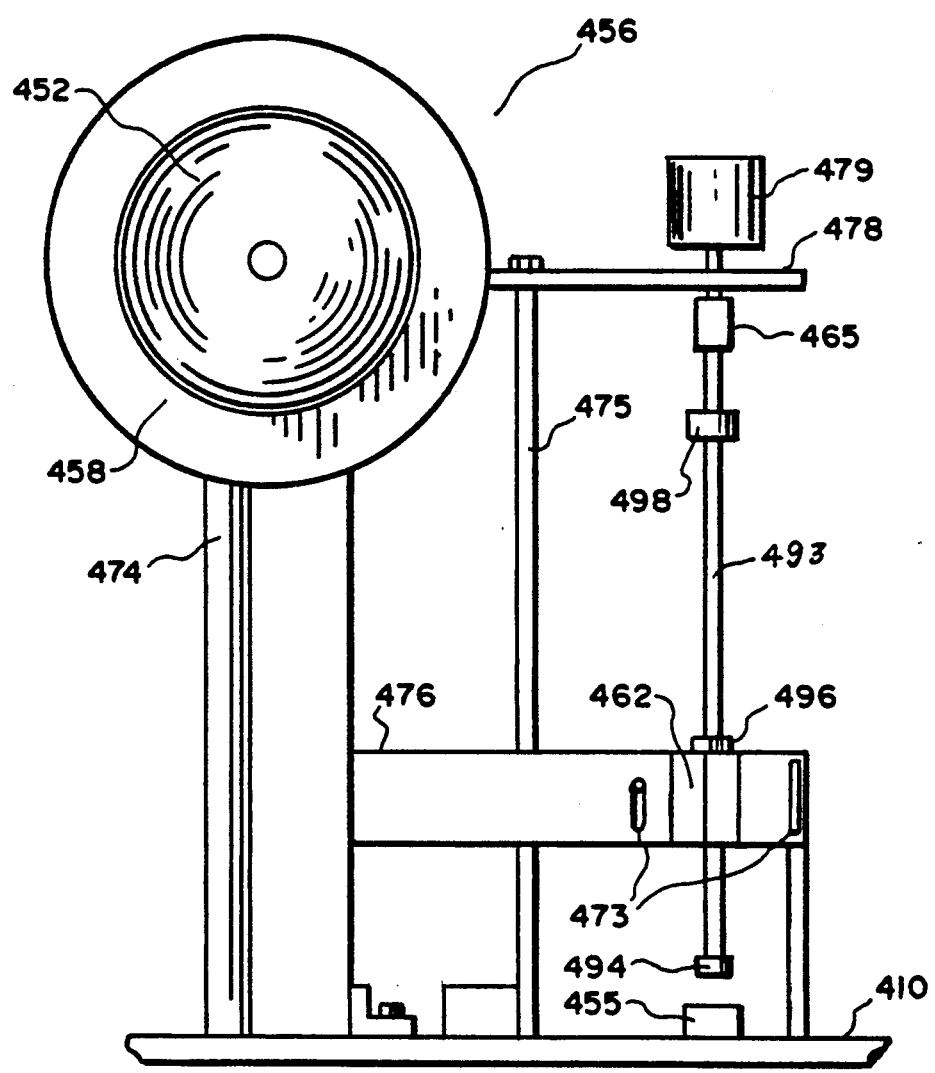
FIG. 31 is a side elevational view of the piston cleaning station embodiment shown in FIG. 25.

The manipulator 402 retrieves the piston rod 493 and transports the piston rod 493 to the piston cleaning station 456 (FIG. 31). The piston cleaning station 456 has a support stand 474 mounted to the table 410 which has fixed to, and extending outwardly from the upper end of the support stand 474, a horizontal support 478. At the distal end of horizontal support 451 is located a motor 479 which is used to drive a piston socket 465. A piston foot cleaning cavity 455 is mounted on the table 410 and is aligned with the piston socket 465. Fixed to, and extending outwardly from the lower half of the support stand 474, is a horizontal support 476 which contains a piston cleaning gripper 462 and multiple guide rollers 473. At the location where the horizontal support 478 is fixed to the support stand 440, a cleaning material source roller 458 and a take up roller 453 are rotatably attached to support stand 474 to supply a cleaning material strip 452 to the piston cleaning station 456. The piston rod 493 is placed into the piston foot cleaning cavity 455 and is held in place by the piston socket 465. The piston cleaning gripper 462 which has the cleaning material strip 452 threaded through the gripper 462 is driven up and down on a threaded shaft 475 by a motor (not shown) and at the same time the piston socket 465 is rotating the piston rod 493. Then a take up roller 453 at the station is operated to move a clean section of strip 452 through the piston cleaning gripper 462. After the piston rod 493 is cleaned, the piston rod 493 is placed in the piston preheat station 490.

The manipulator 402 moves the piston rod 493 from the test station, such as station 1, to the piston cleaning station 456. At the same time, the cleaning rod 450 (FIG. 30) moves down and up in the test sleeve/die insert 440 to clean the inside thereof which formed a test cavity when it was in the heating chamber 431. In this way, the piston rod 493 and the sleeve/die insert 440 are cleaned at the same time.

The cleaning of the sleeve/die insert 440 and the piston rod 493 in this manner allows the manipulator 402 to then go get another sleeve/die insert 440 and move it to another test station to begin another test. In this way testing is not held up by the cleaning functions or the cleaning steps and the foregoing steps are repeated at test station No. 2 and test station No. 3. After a sleeve/die insert 440 has been cleaned, it will be placed in the collection rack 495.

A smaller diameter hole or passage 460 extending through the die 442 (FIG. 26) is cleaned as a combination of the cleaning solvent being pushed down and a rod in the base of the cleaning block 446 which is pushed into the die 442 (FIG. 26) when the sleeve/die insert 440 is placed into the cleaning block 446. The cleaned sleeve/die inserts 440 are collected in rack 495 and manually removed therefrom, refilled with polymer and inserted into another sample rack 438.

In the meantime, when all the sleeve/die inserts 440 containing polymer to be tested have been removed from the rack 438, the rack 438 is withdrawn from the machine 400 and a new rack 438 with a new set of samples in sample sleeve/die inserts 440 is positioned in the machine 400.

The machine 400 also includes a personal computer 470. Also, as shown in FIGS. 27 and 28, the manipulator 402 has a depending tooling arm 480 which has a gripper 482 at the lower end thereof for engaging a sleeve/die insert 440 or a piston rod 493 for lifting same to move it to a station in the machine 400.

Although not shown, a priority sample station can be present on machine 400. When a sleeve/die insert 440 is placed in the priority sample station the manipulator 402 will pick this sleeve/die insert 440 up to run in the next available heating chamber 431, 432 or 433 instead of picking a sample from the sample sleeve rack 438.

EXAMPLE

Flow rate tests were run on a commercially available plastometer and on the automated flow rate machine 400 described above for a 10-5019 grade of polypropylene manufactured by Amoco Chemical Company.

The plastometer had a heating block which was a steel cylinder, 2-inch diameter and 6.375-inch length with a test cavity having a 0.376-inch diameter. Two thermo-wells were provided, one for a thermal sensor and the other for a thermometer. A plate was attached to the bottom of the heating block to retain a steel die which had a straight-bore diameter of 0.0825 inches and a length of 0.315 inches. The surfaces of the test cavity and the die had a finish of 12 RMS.

An automated flow rate machine similar to machine 400 described above had a heating block of an aluminum chrome-plated cylinder, 2-inch diameter and 6.375-inch in length, with a test cavity chamber having a diameter of 0.452 inches. Two thermo-wells were provided for the thermal sensor and a thermometer. A plate was attached to the bottom of the heating block to retain a cylinder sleeve and die. The cylinder sleeve was 6.344 inches in length, 0.437 inches outside diameter, 0.376 inches inside diameter, with 13/32 -24 threads having a depth of 0.2838 inches. The die had a straight bore, 0.0825-inch diameter and 0.315-inch length. The dies can be interchangeable. The cylinder sleeve and die were constructed with chrome-plated aluminum having a 12 RMS finish.

During the evaluation of flow rate tests on the plastometer operated manually and the automated flow rate machine, the same piston, test weight, heating element and temperature controller were used. Ten flow rate tests were run according to ASTM D 1238-86 (Procedure B) on each of the test machines using the 10-5019 grade of polypropylene. The results are given in Table 1 below together with mean value, standard deviation and 95% confidence limit values for ten tests run by each machine.

TABLE I

| Test No. | Flow rate, g/10 min. | |
|---|---|---|
| | Plastometer | Automated Machine |
| 1 | 17.58 | 18.72 |

TABLE I-continued

| Test No. | Flow rate, g/10 min. | |
|---|---|---|
| | Plastometer | Automated Machine |
| 2 | 17.30 | 18.42 |
| 3 | 17.55 | 18.78 |
| 4 | 17.05 | 18.11 |
| 5 | 17.87 | 18.61 |
| 6 | 18.02 | 18.32 |
| 7 | 19.00 | 18.66 |
| 8 | 19.16 | 18.35 |
| 9 | 17.95 | 18.57 |
| 10 | 19.69 | 18.46 |
| Mean Value | 18.42 | 18.50 |
| Standard Deviation | 0.87 | 0.21 |
| Confidence Level (95%), % | 9.4 | 2.2 |

Also, it will be understood that various modifications can be made to the machine 10 or the machine 400 without departing from the teachings of the invention. The embodiment of the invention incorporated into machine 400 can be used to automate other analytical tests such as an alcohol die swell test, dynamic die swell tests and rheological tests run according to ASTM-D 3835. The test equipment used to make the tests described above can use the automatic loading of test samples and cleaning of the test chambers as described for machine 400 above.

The phenomenon of die swell in which a polymer exhibits expansion of the cross-sectional area of the extrudate following extrusion through a die is considered to be a manifestation of the elasticity property of the polymer. Typically, in existing plastometers, the extrudate is placed in a material like alcohol to solidify the polymer at the expansion level achieved at the exit of the die. Measurements can be made on the extrudate diameter and compared to the extrusion die diameter to obtain a measure of the die swell. The extrudate diameter can be measured with machine vision equipment such as the Bulletin 2802 Line Scan Camera of the Allen-Bradley Company of Milwaukee, Wis.

The machine 10 or 400 of the present invention has a number of advantages some of which have been described above and others of which are inherent in the invention. Also, it will be understood that various modifications can be made to the machine 10 or 400 without departing from the teachings of the invention. Accordingly, the scope of the invention is only to be limited as necessary by the accompanying claims.

We claim:

1. An apparatus for automated flow rate measurements of a polymer comprising:
a table;
at least one heating block attached to the table;
a test cavity positioned in the heating block, the test cavity having a cylindrical shape with an upper end of the test cavity defining an orifice for receiving the polymer and a lower end of the test cavity defining an extrusion die;
means for maintaining the heating block at a predetermined temperature;
means for receiving the polymer said means for receiving the polymer being removably attached to said table;
means for transferring the polymer from the polymer receiving means into the test cavity;
a piston rod having an upper collar fixed thereon, a lower knurled collar slidable thereon and a piston foot located at the end of the piston rod opposite to the upper collar;

means for holding and transferring said piston rod between said means for holding and transferring said piston rod and the test cavity;

at least one test weight;

means for holding and transferring said piston rod between said means for holding and transferring said test weight and the piston rod;

means for timing a sequence of stages of the flow rate measurement after the polymer has been received in the test cavity, the piston rod has been transferred to the test cavity, the test weight has been transferred to the piston rod and whereby the test weight acting on the piston rod causes the piston rod to move downwardly through the test cavity and to extrude the polymer through the extrusion die;

means for calculating the flow rate of the thermoplastic from the timed sequence of stages;

means for cleaning the test cavity said means for cleaning the test cavity attached to said table; and means for cleaning the piston rod said means for cleaning the piston rod attached to said table.

2. The apparatus of claim 1 wherein said means for timing the sequence of stages of the flow rate measurement includes means to measure the diameter of the polymer extrudate.

3. The apparatus of claim 1 wherein said means for receiving polymer includes a carrier having a plurality of receptacles for receiving a plurality of samples of polymer to be tested.

4. The apparatus of claim 3 wherein said receptacles for receiving samples of polymer to be tested comprise a plurality of sleeve/die inserts each comprising an upper sleeve portion for receiving a polymer sample and a lower die portion which has a throughbore extending therethrough which is of smaller diameter than the diameter of the inside of the sleeve where the polymer sample is received and which is coaxial with the upper sleeve portion, said sleeve/die insert being receivable in the heating block and defining both said means for receiving polymer and said test cavity.

5. The apparatus of claim 4 wherein said means for transferring polymer from said polymer receiving means into said test cavity includes moving means for moving the sleeve/die insert into said test cavity.

6. The apparatus of claim 5 wherein said means for cleaning said test cavity includes a cleaning block having a cleaning cavity, and said moving means for moving said sleeve/die insert into said heating block is operable to move said sleeve/die insert from said heating block into said cleaning cavity.

7. The apparatus of claim 6 wherein said means for cleaning said test cavity includes a cleaning rod, means for positioning a patch of cleaning material over said sleeve/die insert, and means for moving said cleaning rod down and then up carrying with said means for moving said cleaning rod the patch of cleaning material in and out of the sleeve portion of said sleeve/die insert.

8. The apparatus of claim 7 wherein said means for cleaning said test cavity in said sleeve/die insert includes means for ejecting a quantity of solvent onto the strip of cleaning material that is pushed into the test cavity.

9. The apparatus of claim 5 wherein said moving means comprises a cartesian-movable overhead manipulator.

10. The apparatus of claim 9 wherein said cartesian-movable overhead manipulator is mounted for sliceable movement on two pairs of bars which in turn are mountable on a framework and said apparatus includes drive means for moving each pair of bars thereby to move the cartesian-movable overhead manipulator in either a X-axis direction or a Y-axis direction above the various means of the apparatus.

11. The apparatus of claim 5 wherein said means for cleaning said piston rod includes a cleaning block having a cleaning cavity therein and a strip of cleaning material which is movable over the cleaning cavity to move a clean section of the strip of cleaning material over the cavity prior to movement of the piston rod therein and said means for cleaning said piston rod further includes means for moving said piston rod over said cleaning cavity and means for moving said piston rod down and up with said clean section of the strip of cleaning material in said cleaning cavity.

12. The apparatus of claim 11 wherein said piston rod cleaning means includes means for ejecting onto the piston rod above the cleaning cavity a quantity of cleaning solvent.

13. The apparatus of claim 11 wherein said cleaning material is a cotton material.

14. The apparatus of claim 1 wherein said means for receiving polymer includes a plurality of receptacles which are received in a carousel.

15. The apparatus of claim 14 including means for tapping the carousel to cause particulate polymer material to settle in the receptacles.

16. The apparatus of claim 14 wherein said means for inserting polymer from said polymer receiving means in said heating block includes means for sequentially inserting polymer from receptacles in said carousel into said heating block.

17. The apparatus of claim 16 wherein said means for transferring polymer from said polymer receiving means into said test cavity in said heating block includes means for moving said carousel over said heating block to position one of said receptacles over the test cavity in said heating block and means for tamping polymer particles from a receptacle in said carousel into said test cavity.

18. The apparatus of claim 1 wherein said means for cleaning said piston rod includes a cleaning block with a cleaning cavity therein, means for moving said piston rod from said heating block to a cleaning station and over a clean strip of cleaning material positioned over said cleaning cavity in said cleaning block, and means for moving said piston rod down and up to move the piston rod with the clean strip of cleaning material into and out of the cleaning cavity for cleaning the piston rod and the piston foot.

19. The apparatus of claim 18 wherein said means for cleaning said piston rod includes means for ejecting a quantity of cleaning solvent against the piston rod and above the strip of cleaning material.

20. The apparatus of claim 1 wherein said means for cleaning said test cavity in said heating block includes means for supplying a patch of cleaning material to a position over the test cavity in said heating block, means for moving a cleaning rod over said patch of cleaning material in said test cavity thereby forming a used patch of cleaning material, means for moving said cleaning rod down and up to clean the test cavity in the heating block and means for removing the used patch of cleaning material from the top of said heating block when the cleaning rod has completed its down and up movement and is moved to an up position.

21. The apparatus of claim 20 wherein said means for cleaning said test cavity includes means for ejecting a quantity of cleaning solvent over the patch of cleaning material and on the cleaning rod.

22. The apparatus of claim 20 wherein said means for removing said used patch of cleaning material includes a discharge chute and a fluid ejection means for ejecting a fluid against the used patch of cleaning material to cause same to move through the discharge chute to a receptacle for collecting used patches of cleaning material.

23. The apparatus of claim 1 wherein said means for holding and transferring the test weight between said means for holding and transferring the test weight and said piston rod includes weight holding means for moving said test weight over said piston rod when said piston rod is moved into said test cavity, means for releasing said test weight on said piston rod, means for lowering said weight holding means and means for gripping said test weight and lifting said test weight off of said piston rod.

24. The apparatus of claim 1 wherein said means for holding said piston rod includes means for maintaining said, piston rod at a desired temperature.

25. The apparatus of claim 1 wherein said means for timing the sequence of stages of the flow rate measurement includes a first noncontact switch to indicate that the sequence of stages has started and a second noncontact switch to indicate that the sequence of stages is completed.

26. A method for making automated flow rate measurements of a polymer comprising the steps of:
   maintaining a heating block at a predetermined temperature;
   inserting polymer into a polymer receiving means;
   placing polymer from the polymer receiving means into a test cavity in the heating block;
   moving a piston rod into the test cavity;
   timing a holding period of polymer in the heating block;
   placing a test weight on the piston rod in the test cavity whereby the test weight acting on the piston rod causes the piston rod to move downwardly into the test cavity to move heated polymer therein;
   measuring an amount of time between the beginning of the downward movement of the weighted piston rod and when the weighted piston rod has moved a predetermined distance downwardly into the test cavity;
   calculating the flow rate using the amount of time measured and a factor corresponding to the polymer;
   removing the piston rod from the test cavity;
   cleaning the piston rod; and
   cleaning the test cavity in the heating block to prepare the heating block for another flow rate test.

27. The method of claim 26 wherein said polymer receiving means comprises a sleeve/die insert which has an upper sleeve portion which receives a quantity of polymer and a lower die portion which a smaller diameter throughbore extending therethrough, said sleeve/die insert defining said test cavity in the heating block and said step of placing polymer in the heating block includes the step of placing the sleeve/die insert, defining the test cavity and the polymer receiving means, into the heating block.

28. The method of claim 26 wherein said piston rod has a weight fixed thereon and said step of weighting the piston rod in the test cavity with the weight includes the step of placing the weighted piston rod into the test cavity.

29. The method of claim 26 wherein said step of cleaning said test cavity includes the step of providing a cleaning block having a cleaning cavity therein and the step of moving said sleeve/die insert from said heating block into said cleaning cavity.

30. The method of claim 29 wherein said step of cleaning said test cavity includes the step of positioning a section of a strip of cleaning material over said sleeve/die insert in said cleaning cavity and the step of moving a cleaning rod down and then up carrying with it the section of the strip of cleaning material in and out of the sleeve portion of said sleeve/die insert.

31. The method of claim 30 wherein said step of cleaning said piston rod includes the steps of providing a cleaning block having a cleaning cavity therein, positioning a strip of cleaning material over the cleaning cavity, moving a clean section of the strip of cleaning material over the cavity, moving the piston rod over the cleaning cavity and moving the piston rod down and up with said clean section of the strip in the cleaning cavity.

32. The method of claim 31 wherein said step of cleaning said piston rod includes the step of ejecting onto the piston rod above the cleaning cavity a quantity of cleaning solvent.

33. The method of claim 26 wherein said step of placing polymer from a polymer receiving means into the test cavity in said heating block includes the step of sequentially inserting polymer from receptacles in a carousel into the test cavity in the heating block.

34. The method of claim 33 wherein said step of inserting polymer into said test cavity includes the step of tamping with a tamping rod polymer material from a receptacle in the carousel into the test cavity in the heating block.

35. The method of claim 26 wherein said step of cleaning said test cavity in said heating block includes the step of positioning a patch of cleaning material over the test cavity in the heating block, moving a cleaning rod over the patch of cleaning material in the test cavity, moving the cleaning rod down and up to clean the test cavity and removing the patch of cleaning material from the top of the heating block when movement of the cleaning rod has been completed and the cleaning rod is moved to an up position.

36. The method of claim 35 wherein said step of cleaning said test cavity in said heating block includes the step of ejecting a quantity of cleaning solvent over the patch of cleaning material and on the cleaning rod.

* * * * *